US012102833B2

(12) United States Patent
Gaddam et al.

(10) Patent No.: US 12,102,833 B2
(45) Date of Patent: *Oct. 1, 2024

(54) MEDICAL DEVICE RECHARGING BASED ON PATIENT ACTIVITY

(71) Applicant: Medtronic, Inc., Minneapolis, MN (US)

(72) Inventors: Venkat R. Gaddam, Plymouth, MN (US); Reid K. Bornhoft, Lino Lakes, MN (US); David P. Olson, Minnetrista, MN (US); Leroy L Perz, Maple Grove, MN (US); Mandla Shongwe, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 841 days.

This patent is subject to a terminal disclaimer.

(21) Appl. No.: 17/199,051

(22) Filed: Mar. 11, 2021

(65) Prior Publication Data
US 2021/0196963 A1 Jul. 1, 2021

Related U.S. Application Data

(63) Continuation of application No. 15/601,708, filed on May 22, 2017, now Pat. No. 10,946,206.

(51) Int. Cl.
*A61N 1/378* (2006.01)
*A61N 1/372* (2006.01)

(52) U.S. Cl.
CPC ....... *A61N 1/3787* (2013.01); *A61N 1/37252* (2013.01); *A61N 1/37223* (2013.01)

(58) Field of Classification Search
CPC .......................... A61N 1/3787; A61N 1/37252
See application file for complete search history.

(56) References Cited

U.S. PATENT DOCUMENTS

| 9,211,418 B2 | 12/2015 | Aghassian |
| 10,946,206 B2 * | 3/2021 | Gaddam .............. A61N 1/3787 |

(Continued)

FOREIGN PATENT DOCUMENTS

| EP | 2667939 A1 | 12/2013 |
| EP | 2705876 A1 | 3/2014 |
| WO | 2012102768 A1 | 8/2012 |

OTHER PUBLICATIONS

Patient Letter, Important Medical Device Safety Information, Eon™ Charging System, St. Jude Medical, Jul. 21, 2014, retrieved from https://www.accessdata.fda.gov/scripts/cdrh/cfdocs/cfRES/res.cfm?id=107420, 3 pp.

(Continued)

*Primary Examiner* — William J Levicky
(74) *Attorney, Agent, or Firm* — Shumaker & Sieffert, P.A.

(57) ABSTRACT

Devices, systems, and techniques for controlling charging power transmitted to an implantable medical device during a recharging process based on patient activity are disclosed. Various example techniques include a method comprising receiving, by processing circuitry, an activity signal generated by an implantable medical device and indicative of an activity level of a patient during charging of a rechargeable power source of the implantable medical device implanted in the patient, determining, by the processing circuitry and based on the activity signal, a patient status for the patient during charging of the rechargeable power source, and controlling, by the processing circuitry and based on the patient status, charging of the rechargeable power source of the implantable medical device.

23 Claims, 10 Drawing Sheets

(56) References Cited

U.S. PATENT DOCUMENTS

| | | |
|---|---|---|
| 2005/0043652 A1* | 2/2005 | Lovett .................. A61B 5/1116 |
| | | 600/595 |
| 2008/0300654 A1 | 12/2008 | Lambert et al. |
| 2009/0112291 A1 | 4/2009 | Wahlstrand et al. |
| 2010/0219796 A1 | 9/2010 | Kallmyer |
| 2010/0298910 A1 | 11/2010 | Carbunaru et al. |
| 2011/0071597 A1 | 3/2011 | Aghassian |
| 2011/0178576 A1 | 7/2011 | Aghassian |
| 2011/0278948 A1 | 11/2011 | Forsell |
| 2012/0262108 A1 | 10/2012 | Olson et al. |
| 2013/0096650 A1 | 4/2013 | Aghassian |
| 2014/0163644 A1 | 6/2014 | Scott et al. |
| 2014/0222106 A1 | 8/2014 | Sharma et al. |
| 2018/0333585 A1 | 11/2018 | Gaddam et al. |

OTHER PUBLICATIONS

Physician Letter, Important Medical Device Safety Information, Eon™ Charging System, St. Jude Medical, Jul. 21, 2014, retrieved from https://www.accessdata.fda.gov/scripts/cdrh/cfdocs/cfRES/res.cfm?id=107420, 2 pp.

International Search Report and Written Opinion from International Application No. PCT/US2018/020560, dated May 18, 2018, 11 pp.

Prosecution History from U.S. Appl. No. 15/601,708, dated Jun. 7, 2018 through Nov. 10, 2020, 203 pp.

* cited by examiner

MEDICAL DEVICE RECHARGING BASED ON PATIENT ACTIVITY

This application is a continuation of U.S. patent application Ser. No. 15/601,708, filed May 22, 2017, the entire contents of which are incorporated herein by reference.

TECHNICAL FIELD

The disclosure relates to medical devices and, more particularly, systems and methods for recharging a power source of a medical device.

BACKGROUND

Implantable medical devices may be used to monitor a patient condition and/or deliver therapy to the patient. In short term or chronic uses, implantable medical devices (IMDs) may include a rechargeable power source (e.g., one or more capacitors or rechargeable batteries) that extends the operational life of the medical device to weeks, months, or even years over a non-rechargeable device.

When the energy stored in the rechargeable power source has been depleted, the patient may use an external charging device to recharge the power source of the IMD. Since the rechargeable power source is implanted in the patient and the charging device is external to the patient, this charging process may be referred to as transcutaneous charging. In some examples, transcutaneous charging may be performed via inductive coupling between a primary coil in the charging device and a secondary coil in the implantable medical device. When an electrical current is applied to the primary coil and the primary coil is located near and aligned to the secondary coil, electrical current is induced in the secondary coil within the patient. Therefore, the external charging device does not necessarily need to physically connect with the rechargeable power source for charging to occur.

SUMMARY

In general, the disclosure is directed to devices, systems, and methods for controlling the recharging process and the charging power transmitted to recharge one or more implantable medical devices (IMDs) that include rechargeable power sources. In various examples, an activity signal generated by the one or more IMDs is used to determine a patient status associated with the patient implanted with the IMD(s) undergoing the recharging process. The activity signal may be based on one or more parameters, such as sensed parameters associated with the patient, that are indicative of inactivity of the patient. A determination of inactivity associated with a patient during a recharging process potentially leads to a situation wherein the charging process could result in damage to the tissue of the patient, for example in the area of the IMD(s) and/or the area where the recharging power is being transmitted. A determination of inactivity of the patient may be used to control the recharging process to prevent potential issues related to overheating and potential tissue damage.

In one aspect, the disclosure is directed to a method comprising: receiving, by processing circuitry, an activity signal generated by an implantable medical device and indicative of an activity level of a patient during charging of a rechargeable power source of the implantable medical device implanted in the patient; determining, by the processing circuitry and based on the activity signal, a patient status for the patient during charging of the rechargeable power source; and controlling, by the processing circuitry and based on the patient status, charging of the rechargeable power source of the implantable medical device.

In another aspect, the disclosure is directed to a system comprising: an implantable medical device comprising processing circuitry and a rechargeable power source, wherein the processing circuitry is configured to: receive an activity signal generated by the implantable medical device, the activity signal indicative of an activity level of a patient during charging of the rechargeable power source of the implantable medical device implanted in the patient; determine, based on the activity signal, a patient status for the patient during recharging of the rechargeable power source; and control, based on the patient status, recharging of the rechargeable power source of the implantable medical device.

In another aspect, the disclosure is directed to a system comprising: means for receiving an activity signal generated by an implantable medical device and indicative of an activity of a patient during charging of a rechargeable power source of the implantable medical device implanted in the patient; means for determining, based on the activity signal, a patient status for the patient during charging of the rechargeable power source; and means for controlling, based on the patient status, charging of the rechargeable power source of the implantable medical device.

The details of one or more examples are set forth in the accompanying drawings and the description below. Other features, objects, and advantages will be apparent from the description and drawings, and from the claims.

DETAILED DESCRIPTION

Figure 1:
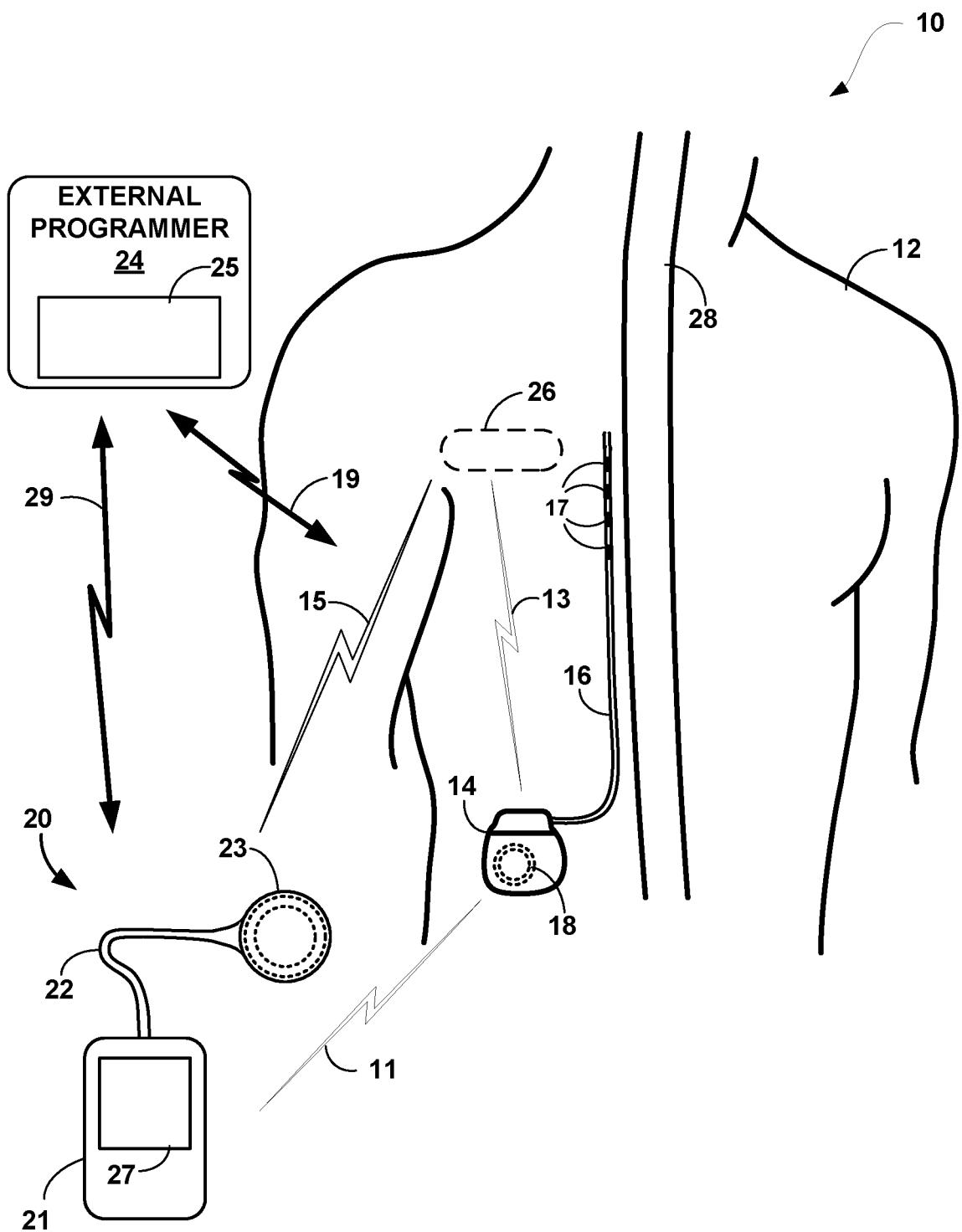
FIG. 1 is a conceptual diagram illustrating an example system that includes an implantable medical device (IMD) and an external charging device that recharges a rechargeable power source of the IMD in accordance with the techniques described in this disclosure.

This disclosure is generally directed to devices, systems, and methods for controlling the recharging process and controlling power levels that may be used to recharge a rechargeable power source of one or more IMDs implanted in a specific patient based at least in part on an activity status of the patient.

Implantable medical devices (IMDs) may be implanted within a patient and used to monitor one or more parameters of the patient and/or to deliver a therapy to the patient. To extend the operational life of the IMDs, each IMD may include a rechargeable power source (e.g., one or more capacitors or batteries). As part of the recharging process, an external charging device may transcutaneously charge the rechargeable power source of the one or more IMDs implanted within a patient. When the rechargeable power source is being recharged, the power transmitted to the IMD may generate heat that increases the temperature of the IMD. In particular, the generated heat may become problematic when the external charging device is positioned between the patient and another object (e.g., a chair or bed) such that the heat is not dissipated quickly. In some examples, in order to prevent increased temperatures associated with the recharging process from damaging patient tissue adjacent to the IMD, charging sessions may be limited to predetermined durations and/or to reduced power levels over some portion of the recharging session used for recharging the rechargeable power source. However, this approach may increase recharge durations and/or prevent the rechargeable power source from being fully charged.

For example, during a recharging process an external charging device may calculate an estimated cumulative thermal dose delivered to the patient during the charging process. A temperature of the IMD, a skin temperature of the patient in the areas where the recharging coils are located, and/or a temperature of the primary coil of the external charging device may be monitored during the recharging process. These and other monitored parameters may be used by the recharging device to modify and control the recharging process, including raising or lowering the power levels being applied to the recharging process used in recharging the power source of the one or more implanted IMDs.

However, in some examples, it may be difficult for the recharging process to be configured or modeled to mitigate some of the end-use conditions that may increase the rate of temperature rise, such as when a patient falls asleep during a recharge session and, for example, the recharger primary coil is positioned between the body and a bed or couch. Such conditions may create a situation wherein the normal dissipation of heat generated at the primary coil to ambient air is not occurring due to the placement of the primary coil between the patient and an insulative layer of material, such as a mattress of the bed or a cushion of the couch where the patient is positioned during the recharging process. If the patient has also fallen asleep in such a position, the patient may not be able to recognize that an overheating condition is occurring due to the placement of the primary coil between the patient and the insulating layer, which may present an increased risk of excess heat delivery to the patient.

The devices, systems, and methods described herein provide targeted solutions for each individual patient, aimed at recognizing the recharge use condition wherein the patient might have fallen asleep, for example either on a bed or a couch, since starting a recharge session. The devices, systems and methods described herein may utilize sensed parameter, such as accelerometer data provided by the implanted medical device and/or other sensors associated with the patient, for indications of certain postures and/or of prolonged periods of inactivity and/or sleep. Additional predefined parameters, such as normal sleep times for the patient, and/or normal geographical locations where the patient normally sleeps, may also be factors that determine the activity level of the specific patient. Based on one or some combination of these sensed and/or predefined parameters, a status, such as an "active" status or an "inactive" status, may be associated with the patient at various times throughout the recharging process. Once a determination is made that an "inactive" status exists for the patient during a recharging process being performed one or more IMDs implanted within the patient, the recharge rate may be further controlled, for example to decrease the induced heat generated by the recharging process. This targeted, adaptive rate recharge solution is specific to the individual patient and may only be triggered upon detecting the status associated with the patient to be an "inactive" status.

The systems, devices, and techniques disclosed herein may reduce the burden on the physician to instruct the patient to follow certain precautions during recharge, may reduce the burden on the patient to follow these precautions, and may reduce the burden on the medical device manufacturer to supplement their product labeling with these precautions. In addition, systems, devices, and techniques disclosed herein provide and additional measure of safety to the patient during the recharging process by monitoring for conditions that potentially could lead to an overheating condition during the recharging process, and providing for further control of the recharging process to prevent the possible overheating from occurring when the conditions are detected.

FIG. 1 is a conceptual diagram illustrating an example system 10 that includes an implantable medical device (IMD) 14 and an external charging device 20 that charges a rechargeable power source 18 of IMD 14. Although the techniques described in this disclosure are generally applicable to a variety of medical devices including medical devices such as patient monitors, electrical stimulators, or drug delivery devices, application of such techniques to implantable neurostimulators will be described for purposes of illustration. More particularly, the disclosure will refer to an implantable neurostimulation system for use in spinal cord stimulation therapy, but without limitation as to other types of medical devices.

As shown in FIG. 1, system 10 includes an IMD 14 and an external charging device 20 shown in conjunction with a patient 12, who is ordinarily a human patient. IMD 14 and external charging device 20 may be communicatively link via communication/power link 11. Examples of system 10 may also include one or more sensors 26, which may be implanted and/or worn by patient 12, and that may be communicatively coupled via communication link 13 with IMD 14. In various examples, sensors 26 may also be communicatively coupled with external charging device 20 via communication link 15. Examples of system 10 may also include an external programmer 24, located externally to patient 12, which is communicatively coupled via communication link 19 to one or more implanted and/or worn devices of system 10. External programmer 24 may also be communicatively coupled to external charging device 20 via communication link 29. As described herein, information may be transmitted between IMD 14 and external charging device 20, between IMD 14 and sensors 26, between sensors 26 and external charging device 20, and between external programmer 24 and IMD 14, sensors 26, and external charging device 20. Any of these communications may be provided via wireless communication using any techniques known in the art. Examples of communication techniques may include, for example, low frequency or radiofrequency (RF) telemetry, but other techniques are also contemplated. In some examples, external charging device 20 may include a communication head that may be placed proximate to the patient's body near the IMD 14 implant site in order to improve the quality or security of communication between IMD 14 and external charging device 20. The communications between external charging device 20 may occur during or separate from power transmission between IMD 14 and external charging device 20.

In the example illustrated in FIG. 1, IMD 14 is an implantable electrical stimulator that delivers neurostimulation therapy to patient 12, e.g., for relief of chronic pain or other symptoms. Generally, IMD 14 may be a chronic electrical stimulator that remains implanted within patient 12 for weeks, months, or even years. In the example of FIG. 1, IMD 14 and lead 16 may be directed to delivering spinal cord stimulation therapy. In other examples, IMD 14 may be a temporary, or trial, stimulator used to screen or evaluate the efficacy of electrical stimulation for chronic therapy. IMD 14 may be implanted in a subcutaneous tissue pocket, within one or more layers of muscle, or other internal location. As illustrated in FIG. 1, IMD 14 includes rechargeable power source 18, and is coupled to lead 16.

As part of system 10, one or more sensors 26 may be located outside of or separately located relative to the IMD 14. These one or more additional sensors 26 are illustratively represented by sensors 26 in FIG. 1. Sensors 26 may include a single sensor circuit configured to sense a particular physiological parameter associated with patient 12, or may comprise a plurality of sensor circuits, which may be located at various and/or different positions relative to patient 12 and/or relative to each other, and are configured to sense one or more physiological parameters associated with patient 12. For example, sensors 26 may include one or more sensors operable to sense a body temperature of patient 12 in a location of the sensor circuits, or at a location of the patient where a temperature sensor is located, the temperature sensor coupled by a lead to sensors 26. In another example, sensors 26 may include sensor circuits configured to sense motion, such as steps taken by patient 12, and/or a current posture of patient 12. In various examples, sensors 26 may include a sensor circuit that is configured to detect breaths taken by patient 12. In various examples, sensors 26 may include a sensor circuit configured to detect heartbeats, e.g., cardiac depolarizations, of patient 12. In various examples, sensors 26 may include one or more sensor circuits that are configured to measure one or more blood pressures, such as systemic and/or pulmonary blood pressures of patient 12. Sensor circuits included in sensors 26 may sense other physiological parameters associated with patient 12, including blood oxygen saturation levels, galvanic skin temperature, a level of a chemical, such as melatonin, that is present in the patient, brain waves (gamma, beta, alpha, theta, and/or delta waves), and other parameters that may be associated with physiological parameters of patient 12.

In some examples, one or more of the sensors 26 comprise sensor circuits that are implanted within patient 12, that is, implanted below at least below the skin level of the patient. In some examples, one or more of the sensors 26 may be located externally to patient 12, for example as part of a cuff or as a wearable device, such as a device imbedded in clothing that is worn by patient 12, and/or may be part of the external charging device 20. In various examples, sensors 26 may be configured to sense one or more physiological parameters associated with patient 12, and to transmit data corresponding to the sensed physiological parameter or parameters to IMD 14, as represented by communication link 13 coupling sensors 26 to IMD 14. Transmission of data from sensors 26 to IMD 14 in various examples may be performed via wireless transmission, as would be understood by those of skill in the art. In various examples, transmission of data from one or more of the sensors 26 may be performed by a wired connection between the sensors 26 and IMD 14. In various examples, signals generated by sensors 26 may also be wirelessly transmitted to external charging device 20, as represented by communication link 15 in FIG. 1, and/or may be wirelessly transmitted to external programmer 24, as represented by communication link 19 in FIG. 1.

IMD 14 may be configured to receive signals, wirelessly and/or through leads or other wired connections, from the sensors 26, the signals indicative of the sensed parameters being measured by the sensor circuits of sensors 26. In various examples, one or more sensed parameters associated with patient 12 may be sensed by sensor(s) and sensor circuits included within IMD 14. For example, IMD may comprise one or more accelerometers or other types of sensors that provide signals indicative of a current posture of patient 12, and/or of motions associated with patient 12. In various examples, IMD 14 includes additional sensors that are configured to sense additional physiological parameters, such as temperature, heartrate, respiratory rates, blood pressure, and/or blood oxygen saturation levels associated with patient 12. In various examples, IMD 14 is configured to receive signals from one or more of these sensors within IMD 14, and/or signals provided by the electrodes 17 on lead 16, and/or signals provided by sensors 26, and in some examples to provide an output signal for example to external charging device 20 and/or external programmer 24, indicative of a posture and/or activity level determined for the patient at various times. In various examples, signals sensed by sensors within IMD 14 and/or by sensors 26 are provided to the external charging device 20 and/or external programmer 24 directly, wherein the external device(s) receive the sensor signals, and determine the current posture and/or the activity level for patient 12 based on the received signals. The signal may be further processed, for example by processor circuitry located in IMD 14, and/or in one or more external devices such as external charging device 20 and/or external programmer 24, to monitor and control a recharging process being performed by system 10 to recharge an implanted rechargeable power source, such as power source 18 of IMD 14. In some examples, the sensor signal may be broadcast, for example using Bluetooth® Low Energy (BLE), at some time interval, for example once a minute, to the external devices, such as external charging device 20 and/or external programmer 24. In these examples, processing circuitry in these external devices may then process these signals to determine the activity status of the patient, and to further control the recharging process based on the sensor signals and/or the determined patient status. In some examples, the processing circuitry of IMD 14 may initially process the sensor signal, for example to the point of determining the patient status based on the sensor signals and/or additional parameters associated with the patient. In these examples, packaged data, for example a data value representative of the patient status, may be communicated from IMD 14 to the external device(s), at some predetermined time interval, for example once every minute.

In various examples, transmission of data from the sensors and/or IMD 14 is triggered by a polling by the external device(s) for the sensor signals and/or data, which may occur at some predefined time interval, such as once every minute, or may occur based on other factors determined by the external device, such as power level, recharging state, and/or temperatures detected by the external device(s) related to the recharging process. Polling as used herein refers to examples where the device performing the polling transmits a request for information to one or more other devices, requesting the one or more other devices respond to the polling request by sending at least a response and/or information back to the device transmitting the request. In non-polling examples, a device may simply transmit data to another device, for example at some predefined time interval, or for example based on some triggering event such as a change in the patient status, without the device that is to receive that transmitted data making a request to have the data transmitted.

In various examples, IMD 14 is configured to provide therapy in the form of electrical stimulation energy to patient 12. The electrical stimulation energy, which may be constant current or constant voltage based pulses, for example, is delivered from IMD 14 to one or more targeted locations within patient 12 via one or more electrodes 17 of lead 16. The parameters for a program that controls delivery of stimulation energy by IMD 14 may include information identifying which electrodes have been selected for delivery of stimulation according to a stimulation program, the polarities of the selected electrodes, i.e., the electrode configuration for the program, and voltage or current amplitude, pulse rate, pulse shape, and pulse width of stimulation delivered by the electrodes. Electrical stimulation may be delivered in the form of stimulation pulses or continuous waveforms, for example.

In the example of FIG. 1, lead 16 is disposed within patient 12, e.g., implanted within patient 12. Lead 16 tunnels through tissue of patient 12 from along spinal cord 28 to a subcutaneous tissue pocket or other internal location where IMD 14 is disposed. Although lead 16 may be a single lead, lead 16 may include a lead extension or other segments that may aid in implantation or positioning of lead 16. In addition, a proximal end of lead 16 may include a connector (not shown) that electrically couples to a header of IMD 14. Although only one lead 16 is shown in FIG. 1, system 10 may include two or more leads, each coupled to IMD 14 and directed to similar or different target tissue sites. For example, multiple leads may be disposed along spinal cord 28 or leads may be directed to spinal cord 28 and/or other locations within patient 12.

Lead 16 may carry one or more electrodes, such as electrodes 17, that are placed adjacent to the target tissue, e.g., spinal cord 28 for spinal cord stimulation (SCS) therapy. One or more electrodes may be disposed at a distal tip of lead 16 and/or at other positions at intermediate points along lead 16, for example. Electrodes 17 of lead 16 transfer electrical stimulation generated by an electrical stimulation generator in IMD 14 to tissue of patient 12. The electrodes may be electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for therapy. In general, ring electrodes arranged at different axial positions at the distal ends of lead 16 will be described for purposes of illustration.

In alternative examples, lead 16 may be configured to deliver stimulation energy generated by IMD 14 to stimulate one or more sacral nerves of patient 12, e.g., sacral nerve stimulation (SNS). SNS may be used to treat patients suffering from any number of pelvic floor disorders such as pain, urinary incontinence, fecal incontinence, sexual dysfunction, or other disorders treatable by targeting one or more sacral nerves. Lead 16 and IMD 14 may also be configured to provide other types of electrical stimulation or drug therapy (e.g., with lead 16 configured as a catheter). For example, lead 16 may be configured to provide deep brain stimulation (DBS), peripheral nerve stimulation (PNS), or other deep tissue or superficial types of electrical stimulation. In other examples, lead 16 may provide one or more sensors configured to allow IMD 14 to monitor one or more parameters of patient 12. The one or more sensors may be provided in addition to, or in place of, therapy delivery by lead 16.

IMD 14 delivers electrical stimulation therapy to patient 12 via selected combinations of electrodes 17 carried by lead 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1, the target tissue for electrical stimulation delivered via lead 16 is tissue proximate spinal cord 28, for example one or more target locations of the dorsal columns or one or more dorsal roots that branch from spinal cord 28. Lead 16 may be introduced into spinal cord 28 via any suitable region, such as the thoracic, cervical or lumbar regions. Stimulation of dorsal columns, dorsal roots, and/or peripheral nerves may, for example, prevent pain signals from traveling through spinal cord 28 and to the brain of the patient. Patient 12 may perceive the interruption of pain signals as a reduction in pain and, therefore, efficacious therapy results. For treatment of other disorders, lead 16 may be introduced at any exterior location of patient 12.

Although lead 16 is described as generally delivering or transmitting electrical stimulation signals, lead 16 may additionally or alternatively transmit electrical signals from patient 12 to IMD 14 for monitoring. For example, IMD 14 may utilize detected nerve impulses to diagnose the condition of patient 12 or adjust the delivered stimulation therapy. Sensed signal provided through lead 16 to IMD 14 may also be processed and used to monitor and control a recharging process being used to recharge the rechargeable power source 18 of IMD 14, as further described in this disclosure. As such, lead 16 may thus be used to transmit electrical signals to and from patient 12.

External programmer 24 may allow a user, such as a clinician or patient 12, to interact with a user interface 25 of an external programmer 24 to program IMD 14, and/or to otherwise interface with system 10. In some examples, user interface 25 may include a display screen configured to display information, such as text and/or graphical information, to the user. In some examples, user interface 25 is an input device, such as a touch screen, that allows a user to provide inputs to the external programmer 24 and thus to system 10. Programming of IMD 14 may refer generally to the generation and transfer of commands, programs, or other information to control the operation of IMD 14. For example, the external programmer 24 may transmit programs, parameter adjustments, program selections, group selections, or other information to control the operation of IMD 14, e.g., by wireless telemetry or wired connection, illustratively shown in FIG. 1 as communication link 19. In addition, in some examples user interface 25 may be used to provide a prompt to patient 12, which may include a visual prompt, and tactile prompt, and/or an audio sound prompt, to query patient 12 regarding whether the patient has fallen asleep during a recharging process, as further described below. In some instances, patient 12 may respond to the prompt by providing an input to user interface 25. In some examples, the response to the prompt is communicated to external charging device 20, and/or to IMD 14, and the receipt the response, or a lack of a response, may be used by system 10 to determine what modifications, if any, should be made to the power level being used during a recharging process of rechargeable power source 18, as further described below.

In some cases, an external programmer 24 may be characterized as a physician or clinician programmer if it is primarily intended for use by a physician or clinician. In other cases, the external programmer 24 may be characterized as a patient programmer if it is primarily intended for use by a patient. A patient programmer is generally accessible to patient 12 and, in many cases, may be a portable device that may accompany the patient throughout the patient's daily routine. For example, external programmer 24 may be a patient's smartphone, a laptop computer, or a personal digital assistance (PDA), which the patient would normally have in the patient's vicinity at most times throughout the day. In general, a physician or clinician programmer may support selection and generation of programs by a clinician for use by IMD 14, whereas a patient programmer may support adjustment and selection of such programs by a patient during ordinary use. In other examples, external charging device 20 may be included, or part of, an external programmer. In this manner, a user may program and charge IMD 14 using one device or multiple devices.

IMD 14 may be constructed of any polymer, metal, or composite material sufficient to house the components of IMD 14 (e.g., components illustrated in FIG. 2) within patient 12. IMD 14 may be constructed with a biocompatible housing, such as titanium or stainless steel, or a polymeric material such as silicone or polyurethane, and surgically implanted at a site in patient 12 near the pelvis, abdomen, or buttocks. The housing of IMD 14 may be configured to provide a hermetic seal for components, such as rechargeable power source 18. In addition, the housing of IMD 14 may be selected of a material that facilitates receiving energy to charge rechargeable power source 18.

As described herein, rechargeable power source 18 may be included within IMD 14. However, in other examples, rechargeable power source 18 could be located external to a housing of IMD 14, separately protected from fluids of patient 12, and electrically coupled to electrical components of IMD 14. This type of configuration of IMD 14 and rechargeable power source 18 may provide implant location flexibility when anatomical space for implantable devices is minimal. In any case, rechargeable power source 18 may provide operational electrical power to one or more components of IMD 14.

Rechargeable power source 18 may include one or more capacitors, batteries, or components (e.g. chemical or electrical energy storage devices). Example batteries may include lithium-based batteries, nickel metal-hydride batteries, or other materials. Rechargeable power source 18 is also rechargeable. In other words, rechargeable power source 18 may be replenished, refilled, or otherwise capable of increasing the amount of energy stored after energy has been depleted. Rechargeable power source 18 may be subjected to numerous discharge and recharge cycles (e.g., hundreds or even thousands of cycles) over the life of rechargeable power source 18 in IMD 14. Rechargeable power source 18 may be recharged when fully depleted or partially depleted.

External charging device 20 may be used to recharge rechargeable power source 18 of IMD 14 when IMD 14 is implanted in patient 12. External charging device 20 may be a hand-held device, a portable device, or a stationary charging system. In any case, external charging device 20 may include components necessary to charge the rechargeable power source 18 through tissue of patient 12. In some examples, external charging device 20 may only perform charging of rechargeable power source 18, which may make the use of external programmer 24 unnecessary in some cases. In some examples, external charging device 20 may also perform charging of other rechargeable power sources, such as rechargeable power sources associated with one or more of sensors 26. In some examples, external charging device 20 may be an external programmer or other device configured to perform additional functions. For example, when embodied as an external programmer, external charging device 20 may transmit programming commands to IMD 14 in addition to being configured to recharge the rechargeable power source 18. In another example, external charging device 20 may communicate with IMD 14 via a communication/power link 11 to transmit and/or receive information related to the recharging of rechargeable power source 18.

As shown in FIG. 1, external charging device 20 includes a charging device housing 21 and an energy transfer device 23 coupled to the charging device housing 21 through cable 22. Charging device housing 21 may contain a controller that controls delivery of recharge energy through energy transfer device 23. In other examples, energy transfer device 23 is located within charging device housing 21 along with the controller such that cable 22 is eliminated. In various examples, external charging device 20 includes a user interface 27. User interface 27 may include a display and/or be configured to allow inputs by a user to be made to the device, and may provide any of the features and functions described above with respect to user interface 25 of external programmer 24. External charging device 20 may be configured to generate electrical power based one or more predefined recharging parameters, wherein the generated electrical power is delivered through cable 22 to the energy transfer device 23. In various examples, energy transfer device 23 includes a coil or other winding of an electrically conductive material that acts as the primary coil configured to provide the electrical energy that may be induced into the secondary coil (not shown in FIG. 1) of IMD 14 for the purpose of recharging the power source 18 of IMD 14.

In various examples, energy transfer device 23 includes the primary coil of external charging device 20, the primary coil provided in a flat shaped configuration that is enclosed in a pad or other material covering the primary coil on all sides of the coil. Because the primary coil and the pad are configured to be flat shape, and may be placed at a distance from the housing 21 of external charging device 20 via the use of cable 22, the energy transfer device 23 may be placed between patient 12 and some other insulative material, such as a mattress or a cushion, in such a manner that patient 12 is lying on or leaning against the energy transfer device 23 without experiencing discomfort. In an alternative example wherein energy transfer device 23 is within charging device housing 21, the housing 21 itself may have a form factor that is designed to be placed proximate to, or against, a surface of patient 12 such that housing 21 containing the energy transfer device is between patient 12 and this other insulative material. In either case, patient 12 may also fall asleep during the recharging process using energy transfer device 23, potentially allowing heat to build up at the site of the energy transfer device 23 and/or housing 21 to an undesirable level. The systems, devices, and methods as further described herein provide for controlling the recharging process when using a device, like external charging device 20 with or without energy transfer device 23, which based on a posture and/or an activity level of patient 12, allows external charging device 20 to prevent the excessing heat buildup as part of the recharging process by, in some instances, automatically lowering or removing the power level provided to energy transfer device 23 when a particular posture and/or activity level associated with patient 12 is detected during the recharging process.

For example, IMD 14 may transmit temperature information of IMD 14 and/or of rechargeable power source 18, information related to the received power during charging, the charge level of rechargeable power source 18, charge depletion rates during use, or any other information related to power consumption and recharging of IMD 14 and rechargeable power source 18. This information may be used by external charging device 20 to control the parameters associated with a recharging process, such as when to initiate a recharging process, a power level applied at various times during the recharging process, and the duration of the recharging process, including control over termination of the recharging process. Alternatively or in addition, external charging device 20 may comprise one or more temperature sensors to monitor temperature related to the transfer of power during charging. In some cases, the temperature sensor(s) may be located proximate energy transfer device 23. In specific examples, the temperature sensor(s) may be used to provide temperature information about a portion of external charging device 20 that comes in contact with, or is proximate to, patient 12.

External charging device 20 and IMD 14 may utilize any wireless power transfer techniques that are capable of recharging the rechargeable power source 18 of IMD 14 when IMD 14 is implanted within patient 12. In one example, system 10 may utilize inductive coupling between a primary coil (not shown in FIG. 1) of external charging device 20 and a secondary coil (not shown in FIG. 1) of IMD 14 coupled to rechargeable power source 18. In inductive coupling, external charging device 20 is placed near implanted IMD 14 such that a primary coil of the external charging device 20 is aligned with, e.g., placed over, the secondary coil of IMD 14. External charging device 20 may then generate an electrical current in the primary coil based on a selected power level for recharging the rechargeable power source 18. As described further below, the power level may be selected to control the temperature of IMD 14 and/or the charge rate of rechargeable power source 18. As also further described below, the power level may be regulated, for example reduced, modulated, or completely removed, based on a detected activity status associated with posture and/or activity level of patient 12.

When a recharging process is underway and some level of recharging power is being applied to the primary coil, and the primary and secondary coils are aligned, the electrical current in the primary coil may magnetically induce an electrical current in the secondary coil within IMD 14. Since the secondary coil is associated with and electrically coupled to rechargeable power source 18, the induced electrical current may be used to increase the voltage, or charge level, of rechargeable power source 18. Although inductive coupling is generally described herein, any type of wireless energy transfer may be used to charge rechargeable power source 18. Communications between IMD 14 and external charging device 20, and power transfers between external charging device 20 and the power sources within IMD 14, are illustratively shown as communication/power link 11 in FIG. 1. Communications between IMD 14 and external charging device 20 may be accomplished using a different set of antennas and/or a different communication format with respect to the coils and format(s) used to provide the electrical energy providing the power transfer between the IMD 14 and the external charging device 20 for the recharging process. In some examples, at least some of the communications between IMD 14 and external charging device 20 may be accomplished using the same primary coil and the same secondary coil as antennas for the communication as are used for transferring the electrical energy between IMD 14 and external charging device 20 during the recharging process.

During the energy transfer process that charges rechargeable power source 18, some of the energy may be converted into heat at rechargeable power source 18 and/or other components of IMD 14. Heat may also be generated in the tissue of patient 12 surrounding IMD 14, and by the primary coil, as part of the recharging process. When increased energy levels are used to charge rechargeable power source 18 at a higher rate, the temperature of IMD 14 portions of external charging device 20, and/or the tissue temperatures may also increase. Although the temperature of the IMD 14 housing and/or external charging device 20 may not achieve a temperature sufficient to burn or necrose tissue adjacent to the housing of IMD 14, elevated temperatures may be undesirable and uncomfortable over time. Therefore, external charging device 20 may control the power levels used to charge rechargeable power source 18 to reduce or minimize any undesirable temperatures of IMD 14 that could be caused by charging rechargeable power source 18. In addition, monitoring the temperature of IMD 14 and/or the temperature of tissue adjacent to the housing of IMD 14 may minimize patient discomfort during the recharging process.

As previously mentioned, regulation of the charging process between external charging device 20 and IMD 14 may be based on various parameters using a model, such as a predicative bio-thermal Finite Element Analysis (FEA) model, that evaluates the transient rise in temperature during the charging process. In one example, the power level used by external charging device 20 to charge rechargeable power source 18 may be selected or controlled based on a cumulative thermal dose delivered to patient 12 by IMD 14. The tissue temperature used to calculate the cumulative thermal dose may be determined using several different techniques. Each technique may result in a cumulative thermal dose that estimates the actual cumulative thermal dose received by patient 12.

In another example, the tissue temperature may be indirectly calculated, or estimated, based on a tissue model and the power transmitted to rechargeable power source 18 over a period of time. External charging device 20 may monitor the generated current in the primary coil and the resulting power transmitted from external charging device 20 to the secondary coil located in IMD 14. The transmitted power may be calculated using the generated electrical current, estimated based on the generated electrical current and expected energy losses due to heat and misalignment, estimated based on the generated electrical current and energy losses due to misalignment, or some combination therein. In this manner, external charging device 20 may unilaterally determine the tissue temperature. Alternatively, IMD 14 may measure the actual electrical current induced in the secondary coil coupled to rechargeable power source 18. Based on this measured current, a processor of IMD 14 may calculate the power transmitted from external charging device 20.

IMD 14 may then transmit the calculated power transmitted from external charging device 20 back to external charging device 20.

However, as described above, one or more end use conditions that may occur during the recharging process are not necessarily considered by the model and/or the thermal dose calculations, and in some examples these end use conditions may change, for example increase, the rate of temperature rise of the IMD and/or the tissue surrounding the IMD during the recharging process for any given power level being used. For example, if the primary coil of the external charging device 20 is placed between the patient 12 and another insulative object, such as a mattress, a pad, or cushion of a bed, a chair, or a couch, the heat generated at the primary coil and/or the heat generated within the tissue of the patient adjacent to the IMD and/or the primary coil may not be able to radiate the expected amount of heat to ambient air. This situation could arise for example when a patient has initiated a recharging process, and then falls asleep on the device comprising the primary coil of the external charging device, such that the primary coil is located between the patient and another insulative object, such as a bed mattress or a pad or cushion of a couch where the patient is positioned. Any heat generated at the primary coil, or for example in the tissue of the patient in the area of the primary coil, may be trapped between the patient and for example the mattress or cushion, and may result in a rise in the temperate associated with the charging process that is not necessarily compensated for by the charging and/or tissue model(s) being used to calculate the thermal dose, or otherwise regulate the recharging process. In addition, temperature sensor within the IMD may not detect, or detect at any early stage, the increase in temperature occurring at the primary coil and/or in the patient in areas adjacent to the primary coil under these conditions.

To address these additional end use conditions, examples of the systems, devices, and methods as disclosed herein are configured to determine an activity status, based for example on a posture and/or an activity level associated with the patient 12, during a recharging process, and to further control the recharging process based on the activity status in order to further regulate the recharging process and prevent an overheating situation in instances wherein the patient may have fallen asleep lying on the primary coil during the recharging process. In various examples described in this disclosure, once a relevant posture and/or activity level have been detected that is deemed as an "inactive" status for a patient during a recharging process, in some examples the recharging process may be modified in some manner, for example by modulation of the power being provided during the charging process, to modify and/or lower the power settings used for the recharging process, and/or to terminate the recharging process. In some examples, the adjustments to the recharging process are made automatically, and without the need for prompting to, or any input from, the patient. In other examples, the adjustments to the recharging process may be made based on a lack of a confirmation from the patient, for example that could be provided through external programmer 24, after a prompt regarding the position and/or activity level has been provided by one or more devices of system 10, the confirmation indicating that the patient is not asleep.

In various examples, the determination related to the posture and/or activity level of patient 12 may be based on one or more sensed parameters. For example, IMD 14 may comprise one or more accelerometers, gyroscopes, or other sensors (not specifically shown in FIG. 1) configured to provide output signals indicative of the orientation, e.g., posture, of patient 12. These sensor output signal(s) may be used to determine a current posture for patient 12, such as when patient 12 is laying down and in a face up orientation. In such examples, IMD 14 may be positioned within patient 12 in a location wherein patient 12 normally places the primary coil of external charging device 20 on the patient's back during the recharging process. Having this specific information related to patient 12, and determining that patient 12 is in fact lying down in a face up position during a recharging process, makes it likely that the patient is lying on a pad or other device comprising the primary coil of the recharging device, and that the coil is supported by some other object on the side opposite patient 12, such as a mattress or a cushion. In some examples, one or more of these particular postures, when detected for a specific patient, may be determined to be positons that are predefined as an "inactive posture," which may dictate use of a modified recharging process to prevent possible overtemperature or other unsafe conditions related to the patient 12 and the recharging process.

In various examples, in addition to sensors used to determine a current posture for patient 12, one or more sensors may be used to sense parameters that may be used to determine an activity level for patient 12. For example, the above described signals provided by accelerometers sensing patient posture and/or motion may be used to determine that patient 12 is standing or sitting in an upright position. If these particular postures are detected as the current posture for patient 12 during the time period when a recharging process of IMD 14 is underway, it may indicate that patient 12 is active, or at least is not likely to be sleeping, and therefore further modification to the power levels being applied to the charging process based at least on the detected current posture may not be required.

In various examples, a detected posture associated with patient 12 during the recharging process may be combined with other sensed parameters to determine the activity level of patient 12. For example, the above-mentioned accelerometer signals provided by accelerometer(s) included within IMD 14 or included in sensors 26 may be used to determine a current posture of patient 12, along with a level of activity of patient 12. For example, the accelerometer signals may be used to determine that patient 12 is in a lying down posture. The accelerometer signals may also be analyzed over a period of time, for example over a time period defined by a sliding window of time occurring prior to the current time, to determine an activity level of patient 12. In some examples, if during the sliding window of time, patient 12 is determined to be in the lying down posture and the accelerometers signals also indicate a lack of activity, such as movement, of patient 12, the combination of the current posture and the lack of activity may be used to make a determination that patient 12 has likely fallen asleep. The determination that patient 12 has likely fallen asleep may be used to determine that a status for the patient is in "inactive" status, which may then trigger a modification of the power level being applies to any recharging process currently underway that is being used to recharge power source 18 of IMD 14.

In addition to the accelerometer signals, additional sensor signals generated by sensors within IMD 14 and/or as provided by sensors 26, may be used to monitor one or more physiological parameters of the patient 12. Examples physiological parameters that may be monitored include activity level related to posture (e.g. transitions between defined postures, or velocities associated with patient motions), heart rate, respiration rate, respiratory volume, blood pressure, blood oxygen saturation, partial pressure of oxygen within blood, partial pressure of oxygen within cerebrospinal fluid, muscular activity, core temperature, arterial blood flow, melatonin level within one or more bodily fluids, galvanic skin response, and sensed brain waves (e.g., gamma, beta, alpha, theta, delta waves). In order to monitor one or more of these parameters, IMD 14 and/or external charging device 20 may include and/or be communicatively coupled to the one or more sensors, such as sensors 26, each of which generates a signal as a function of one or more of these physiological parameters associated with patient 12.

In some examples, target threshold values may be defined for these sensed parameters that are specific to patient 12, and the monitored signals may be compared to these target threshold values to make the determination that patient 12 is inactive, and thus may be asleep. For example, a threshold heartrate and a threshold respiration rate may be set for patient 12 relative to whether patient 12 is sleeping. During a recharging process, and for example if a lying down posture is detected as the current posture for patient 12, sensed parameters associated with the heartrate and the respiration rate for patient 12 are monitored. If the monitored heart rate drops below a pre-defined threshold heart rate, and the monitored respiration rate drops below a pre-defined threshold respiration rate set for patient 12, the patient is considered to be asleep, and an activity status of "inactive" may be assigned for the activity level of patient 12 at that time. In another example sensed brain waves may be monitored and analyzed, for example by picking out the bands and levels that would be indicate cognitive function, activity, and/or sleep, and based at least in part on the analysis of these sensed brain waves, determining a status of the patient.

Based on the detected current posture and/or the status of "inactive" determined for patient 12 during a recharging process, the power levels being applied to the charging process may be in some examples be modified, for example by lowering, modulating, or completely removing the power being applied to the recharging process by external charging device 20. In other examples, one or more devices of system 10 may be configured to generate and transmit, for example to external programmer 24, a signal indicative of the determination that the patient status is now considered to be "inactive." The signal indicative of the inactive status may be used to prompt patient 12, for example via a visual, tactile, and/or audio alert provided by external programmer 24. A timer may begin timing once the signal to prompt the patient has been issued, and if at the end of a predefined time period tracked by the timer, the patient had not provided a response of some type to the prompt, the patient is then considered to likely be asleep. In response to this lack of response to the prompt by the patient, the power levels being applied to the charging process may be in some examples modified, for example by lowering, modulating, or completely removing the power being applied to the recharging process by external charging device 20.

Other sensed parameter used to determine a status of patient 12 may include for example use of geo-fencing as a monitored parameter during recharging processes. For example, sensors included within IMD 14, in external charging device 20, and/or otherwise coupled to patient 12 may be configured to provide geographic location information for patient 12. For example, one or more of these sensors may be configured to provide information indicative of a location of patient 12, for example based on a Global Positioning System (GPS) based method. The determined geographic position of patient 12 may be compared to geographic areas designated as sleep areas for patient 12, e.g., as areas indicated to be places where patient 12 normally sleeps. For example, a bedroom where patient 12 normally sleeps can be defined to be within a geo-fenced area designated as a patient sleep area for patient 12. If during a recharging process, patient 12 is determined to be located within one of the geo-fenced areas designed as a sleep area for the patient, IMD, sensors 26, and/or external devices such as external charging device 20 may be configured to begin monitoring the patient to determine additional parameters associated with the patient, such as a current posture, and/or an activity level of the patient. These monitored parameters may be used as described throughout this disclosure to determine an activity level, and to assign an activity status, such as "active" or "inactive" for patient 12. Based on the determined status for patient 12, modifications to the power level being applied to a recharging process that is underway for recharging the power source for IMD 14 may be made, in some examples at least while the patient 12 remains with the geo-fenced area defined as a sleep area for the patient.

In some examples, one or more predetermined parameters associated with patient 12 may be used in determining an activity level for patient 12. For example, a range of times during the day when patient 12 normally sleeps may be stored in one or more devices of system 10, for example in memory (not shown in FIG. 1) included in IMD 14. In some examples, the predetermined parameter may be used to determine if modification of the charging process needs to be considered based on an activity level determined for patient 12. If a recharging process is in process, and for example the time of day falls within the time range indicated as normal sleeping times for patient 12, then one or more sensed parameters may be monitored, for example heart rate and/or respiration rate of patient 12, to determine if the patient is likely to have fallen asleep. In the alternate, if the recharging process is being performed during hours that are not indicated to be normal sleeping hours for patient 12, then the monitoring of the additional sensed parameters used to determine if patient 12 is asleep may not be performed, or a different set of parameters may be monitored based on the current time being outside the normal range of times indicated as sleep times specifically for patient 12. In some examples, stored data activity from the implanted device may be used to learn more and determine patterns for sleeping habits of the patient, that may then be an additional parameter for use in the determination of the activity level of the patient.

In addition to monitoring parameters to determine if patient 12 is likely asleep, patient 12 may provide inputs to system 10, for example through user interface 25 of external programmer 24, indicating that the patient is in fact attempting to fall asleep. For example, the external charging device 20 and/or IMD 14 may receive an indication from the patient that the patient is trying to fall asleep, e.g., via inputs made by the patient to external programmer 24 and communicatively sent to external charging device 20 and/or IMD 14. In other embodiments, sensors of system 10 may monitor the activity level of the patient, and the time when the patient is attempting to fall asleep may be identified by determining whether the patient has remained inactive for a threshold period of time, and identifying the time at which the patient became inactive. In still other embodiments, the sensor 26 of system 10 may monitor patient posture, and one or more processors of IMD 14 and/or external charging device 20 may identify the time when the patient is recumbent, e.g., lying down, as the time when the patient is attempting to fall asleep. In these embodiments, the medical device may also monitor patient activity, and either the implanted medical device 14 or the programming device 24 may confirm that the patient is attempting to sleep based on the patient's activity level determined as described herein.

As another example, one or more sensors of system 10 may determine the time at which the patient begins attempting to fall asleep based on the level of melatonin within one or more bodily fluids, such as the patient's blood, cerebrospinal fluid (CSF), or interstitial fluid. The medical device may also determine a melatonin level based on metabolites of melatonin located in the saliva or urine of the patient. Melatonin is a hormone secreted by the pineal gland into the bloodstream and the CSF as a function of exposure of the optic nerve to light, which synchronizes the patient's circadian rhythm. In particular, increased levels of melatonin during evening hours may cause physiological changes in the patient, which, in turn, may cause the patient to attempt to fall asleep. One or more sensors of system 10 may for example detect an increase in the level of melatonin, and estimate the time that the patient will attempt to fall asleep based on the detection. Brain wave activity may also be monitored in some examples, and used as a basis to determine if the patient is likely to be asleep.

Thus, the time at which the patient has likely fallen asleep may be determined based on the activity level of the patient and/or one or more of the other physiological parameters that may be monitored by the devices of system 10 as indicated above. For example, a discernable change, e.g., a decrease, in one or more physiological parameters, or the variability of one or more physiological parameters, may indicate that the patient has fallen asleep. In some embodiments, a sleep probability metric value may be determined based on a value of a physiological parameter monitored by the sensors as described above. In such embodiments, the sleep probability metric value may be compared to a threshold to identify when the patient has fallen asleep. In some embodiments, a plurality of sleep probability metric values are determined based on a value of each of a plurality of physiological parameters, the sleep probability values are averaged or otherwise combined to provide an overall sleep probability metric value, and the overall sleep probability metric value is compared to a threshold to identify the time that the patient falls asleep. A determination that the patient has fallen asleep based on any of the techniques described above may be used as one or more of the parameters used to determine an activity level associated with patient 12 during a recharging process involving recharging of implanted devices within the patient.

In response to a determination of an "active" or an "inactive" status for patient 12 during a recharging process, the external charging device 20 is configured to control the recharging process, for example the recharging of rechargeable power source 18 of IMD 14, by applying different levels of power to the primary coil of the external charging device 20. For example, a "high" power level, a "medium" power level, and a "low" power level may represent subjective and relative power levels used as the charging power that external charging device 20 is capable of generating and transmitting to IMD 14. In some cases, the "high" power level may be the maximum power that external charging device 20 can generate. This "high" power level may be referred to as a "boost" or "accelerated" charging level because of the high rate of charge induced in rechargeable power source 18. This high rate of charge may minimize the amount of time patient 12 needs to recharge rechargeable power source 18.

During portion of the recharging process when the patient status is determined to "active," by monitoring the cumulative thermal dose, external charging device 20 may charge rechargeable power source 18 with the "high" power level for a longer period of time without damaging tissue surrounding IMD 14. In one example, the "high" power level may be approximately 2.5 Watts, the "medium" power level may be approximately 1.5 Watts and the "low" power level may be approximately 1.0 milliwatts (mW). An example charge current level may be approximately 100 milliamps (mA) for the "high" power level, approximately 80 mA for the "medium" power level, and approximately 60 mA for the low power level. The power level and charge current levels may be determined via predictive Finite Element Analysis (FEA), and are generally dependent on the thermal mass of the implanted device. Smaller devices will generally have smaller power levels and lower charge current levels. For example, smaller devices, e.g., around 3 cc size devices, may use values of around 1.0 Watts, 0.6 Watts, and 0.3 Watts for the high, medium, and low power levels respectively, using charge currents of around 50 mA, 30 mA, and 15 mA, for the high, medium, and low power levels respectively. These values are merely examples, and other examples may include higher or lower values in accordance with the techniques described herein. The frequency of the charging signal may be independent of the power level, and in some examples is based on a fixed frequency to which the recharging system is tuned to in order to maximize one more parameters associated with the efficiency of the recharging process.

In various examples, when the devices of system 10 are performing a recharging process and an "active" status is determined to exist for patient 12, the power level being applied to the recharging process at any given time may be regulated between the "high" power level, the "medium" power level based on various parameters, such as the thermal dose threshold, sensed temperatures of the IMD 14, rechargeable power source 18, tissue of the patient 12, and/or of the primary coil of the external charging device 20. The thermal dose threshold may be the maximum cumulative thermal dose identified as still being safe to patient 12. In other words, the thermal dose threshold may be established or selected to prevent tissue from being heated to an elevated level and duration that could be uncomfortable or undesirable. The thermal dose threshold may be preset by the manufacturer or selected by a clinician. The thermal dose threshold may also be modified over time as needed. In some examples, the thermal dose threshold may not be set to the maximum safe dose. Instead, the thermal dose threshold may be set to a lower value to establish a safety margin below the thermal dose threshold that minimizes potential overheating of tissue.

Although external charging device 20 may select between two power levels based on the cumulative thermal dose, external charging device 20 may select between three or more discrete power levels or select the power level from a continual range of available power levels. For example, external charging device 20 may select between a high, medium, low, and zero (e.g., no transmitted power) power levels to minimize charging times and minimize uncomfortable or undesirable temperatures in surrounding tissue. In another example, external charging device 20 may continually adjust the power level in small increments, where the increments are established by the available resolution of the current able to be generated in the primary coil of external charging device 20. Therefore, these more adjustable power levels may result in a power level curve over time as opposed to individual steps in power levels that would be present using only high, medium, and low power levels. In any example, the transmitted power from external charging device 20 to IMD 14 may be varied based on the calculated cumulative thermal dose.

In another example, external charging device 20 may select a "zero" power level when the cumulative thermal dose has exceeded the thermal dose threshold. This "zero" power level would stop charging rechargeable power source 18 because external charging device 20 would terminate current to the primary coil in response to the selection of the "zero" power level. Although low power levels may be used to recharge the rechargeable power source 18 at low rates (e.g., a trickle charge), terminating charging with the "zero" power level may allow IMD 14 to cool down at the fastest rate and minimize any additional heating of the tissue surrounding IMD 14. In addition, the "zero" power level may be selected when rechargeable power source 18 has been fully charged.

Throughout the recharging process, the devices of system 10 may also monitor patient 12 to determine an activity status for the patient, based for example on a current posture and/or an activity level associated with patient 12. As described above, the current posture and/or the activity level of patient 12 may be determined based on one or more sensed and predetermined parameters associated with the patient. For certain detected current postures, and/or for certain determined activity level(s) determined to exist at some time during the recharging process for patient 12, the devices of system 10 may determine that an "inactive" status for patient 12 has been detected. Based on the "inactive" status being determined as the current status for patient 12, the devices of system 10 may modify the power level of the recharging process to protect patient 12 from a potentially unsafe overtemperature condition that is not necessary contemplated for by the other calculations and/or modeling being used to control the power level of the recharging process for patient 12.

In some examples, a determination of an "inactive" status associated with patient 12 during a recharging process may automatically result in a reduction of the overall power level being applied to the recharging process. In some examples, this reduction in the overall power level may be achieved by reducing the power level being applied to the recharging process to the "low" power level described above. In some examples, this reduction in the overall power level may be achieved by removing the power altogether, (i.e., applying the "zero" power level) being applied to the recharging process. In some examples, reduction of the power level to the "zero" power level may be made either on a temporarily or on a permanent basis. The application of the "zero" power level on a temporary basis may include removing power from the primary coil of external charging device 20 for some predefined time period, and then reapplying power at some other power level, such as the "low" power level. The application of the "zero" power level on a permanent basis may include removing power from the primary coil and terminating the recharging process, wherein initiating or re-initiating another recharging process requires inputs from the patient 12 and/or some other authored input to system 10 requesting initiation of another recharging process associated with the implanted device(s) within or otherwise associated with patient 12.

In some examples, a determination of an "inactive" status for patient 12 during a recharging process will cause at least one of the devices of system 10, such as IMD 14 and/or external charging device 20, to generate and transmit a prompt signal to an external device, such as the external programmer 24. The prompt signal is designed to request, via visual, tactile, and/or an audio prompt provided to the patient, a response indicating that the patient is awake. If response is not received back from the external device, for example within a predefined time limit from the time the prompt signal was issued, the devices of system 10, such as external charging device 20, may reduce the power level or remove power altogether that is being applied to the recharging process. If a response is received back from the external device in reply to the prompt signal, in some examples the power level being provided to the recharging process may not be reduced, at least not at that time, in response to the "inactive" status being detected with respect a current status for patient 12. These and other aspects of the systems, devices, and techniques according to various examples are described below in conjunction with the additional figures of the present disclosure. In various examples, the sensor signals and/or parameter values are received by processing circuitry included within IMD 14, and analyzed by that processing circuitry to determine the patient status, e.g., an "active" or "inactive" patient status. In some examples, data related to the sensor signal and/or other parameters is transmitted to processing circuitry located in one or more external devices, such as external charging device 20, and the determination of the patient status may be made by processing circuitry in the external device(s). Transmission of data from the sensors and/or other related data to the external device(s) may be trigger by a polling request made by the external device(s), and/or by transmission of the data made without a polling request, for example at some regular time intervals, as further described below.

Figure 2:
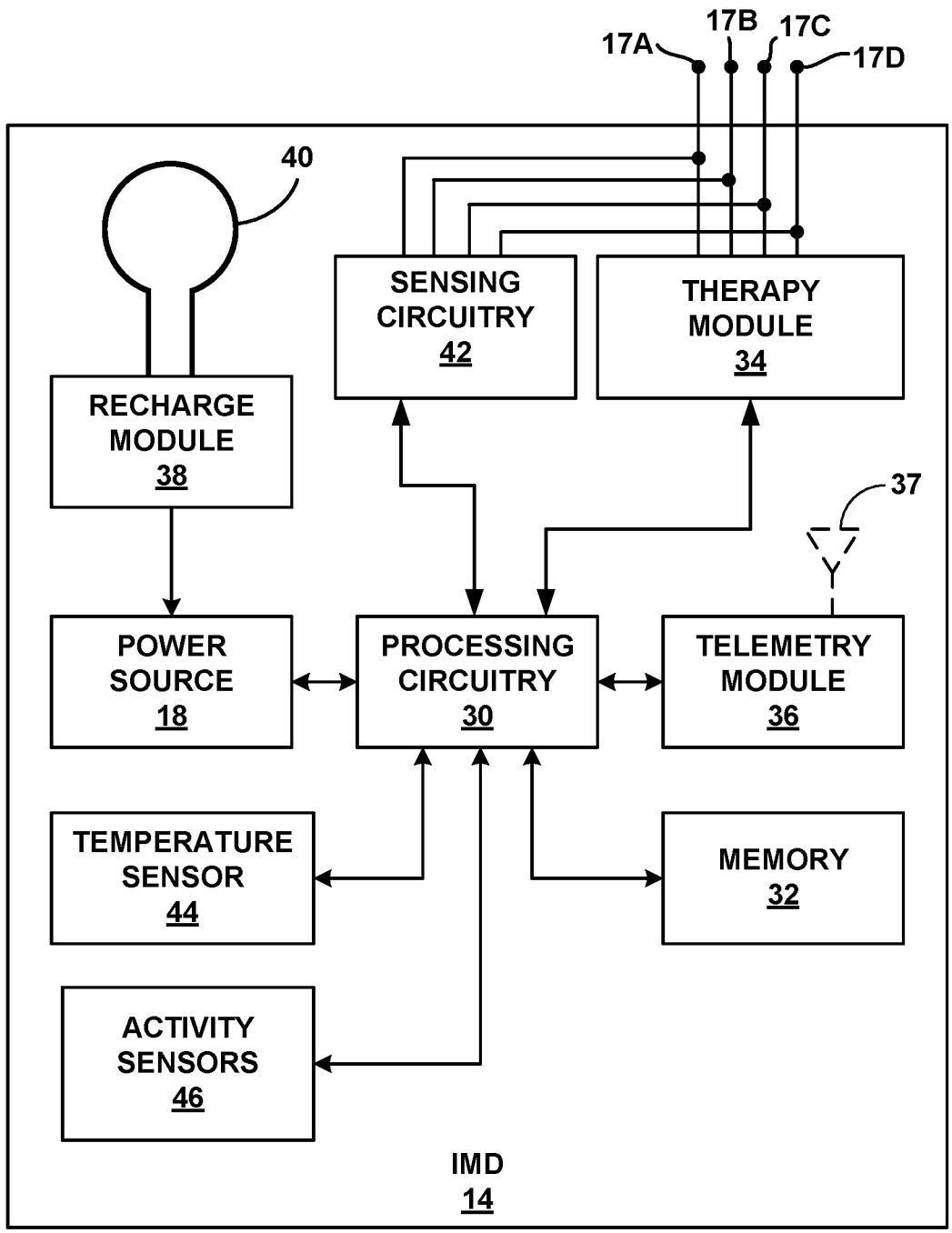
FIG. 2 is a block diagram of the example IMD of FIG. 1.

FIG. 2 is a block diagram illustrating example components of IMD 14. In the example illustrated in FIG. 2, IMD 14 includes processing circuitry 30, memory 32, therapy module 34, telemetry module 36, recharge module 38, sensing circuitry 42, temperature sensor 44, and activity sensors 46. IMD 14 also includes the rechargeable power source 18. In other examples, IMD 14 may include a greater or fewer number of components. In some examples, such as examples in which the tissue temperature is calculated from the transmitted power, IMD 14 may not include temperature sensor 44. In some examples, IMD 14 may be a monitoring device, and may not include therapy module 34.

In general, IMD 14 may comprise any suitable arrangement of hardware, alone or in combination with software and/or firmware, to perform the various techniques described herein attributed to IMD 14 and processing circuitry 30. In various examples, processing circuitry 30 of IMD 14 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 14 also, in various examples, may include a memory 32, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although processing circuitry 30, memory 32, therapy module 34, telemetry module 36, recharge module 38, sensor circuitry 42, temperature sensor 44, and activity sensors 46 are described as separate modules or circuits, in some examples, one or more of these modules and/or circuits are functionally integrated.

In some examples, processing circuitry 30, therapy module 34, telemetry module 36, recharge module 38, sensing circuitry 42, temperature sensor 44 and activity sensors 46 correspond to individual hardware units, such as ASICs, DSPs, FPGAs, or other hardware units. Each of sensors including in sensing circuitry 42, temperature sensor 44, activity sensors 46, and/or sensors 26 generates a signal as a function of one or more physiological parameters of patient 12. IMD 14 may include circuitry (not shown) that conditions the signals generated by the sensors such that they may be analyzed by processing circuitry 30. For example, IMD 14 may include one or more analog to digital converters to convert analog signals generated by these sensors into digital signals usable by processing circuitry 30, as well as suitable filter and amplifier circuitry. IMD may include any number of sensors.

Memory 32 may store therapy programs or other instructions that specify therapy parameter values for the therapy provided by therapy module 34 and IMD 14. In some examples, memory 32 may also stores temperature data from temperature sensor 44, accelerometer data from accelerometer(s) or other sensors included in activity sensors 46, and/or data derived from sensing circuitry 42. In some examples, memory 32 stores instructions for recharging rechargeable power source 18, threshold values, and instructions for communication between IMD 14, external charging device 20, and/or external programmer 24, or any other instructions required to perform tasks attributed to IMD 14.

In this manner, memory 32 may be configured to store information related to determining a status, such as "active" or "inactive" associated with patient 12 during the recharging processes involving IMD 14. Memory 32 may also be configured to store information related to controlling recharging of power source 18 during a recharging process being performed to recharge the rechargeable power source 18. Processing circuitry 30 may be configured to access the information stored in memory 32, and for example in conjunction with sensed values provided by one or more of sensing circuitry 42, temperature sensor 44, sensors of activity sensors 46, and/or additional data received through telemetry module 36, to determine a status of a patient during a recharging process involving devices implanted within the patient, to control the recharging process based at least in part on these status determinations. The additional data received through telemetry module 36 may include signals and/or data generated by sensors outside IMD 14, for example sensors 26 illustrated and described with respect to FIG. 1.

Referring again to FIG. 2, in various examples therapy module 34 may generate and deliver electrical stimulation under the control of processing circuitry 30. In some examples, processing circuitry 30 controls therapy module 34 by accessing memory 32 to selectively access and load at least one of the stimulation programs to therapy module 34. For example, in operation, processing circuitry 30 may access memory 32 to load one of the stimulation programs to therapy module 34. In such examples, relevant stimulation parameters may include a voltage amplitude, a current amplitude, a pulse rate, a pulse width, a duty cycle, or the combination of electrodes 17A, 17B, 17C, and 17D that therapy module 34 uses to deliver the electrical stimulation signal. Although therapy module 34 may be configured to generate and deliver electrical stimulation therapy via one or more of electrodes 17A, 17B, 17C, and 17D of lead 16, therapy module 34 may be configured to provide different therapy to patient 12. For example, therapy module 34 may be configured to deliver drug delivery therapy via a catheter. These and other therapies may be provided by IMD 14.

IMD 14 also includes components to receive power from external charging device 20 to recharge the rechargeable power source 18 when rechargeable power source 18 has been at least partially depleted. As shown in FIG. 2, IMD 14 includes secondary coil 40 and recharge module 38 coupled to rechargeable power source 18. Recharge module 38 may be configured to recharge the rechargeable power source 18 with the selected power level determined by either processing circuitry 30 or external charging device 20. Although processing circuitry 30 may provide some commands to recharge module 38 in some examples, processing circuitry 30 may not need to control any aspect of recharging. For example, processing circuitry 30 may be configured to provide an output signal, for example sensed values and/or alert signals based on the sensed values, to an external charging device, such as external charging devices 20 shown in FIG. 1, wherein the external charging device is configured to control and modify the recharging process based on the information received from IMD 14.

Figure 3:
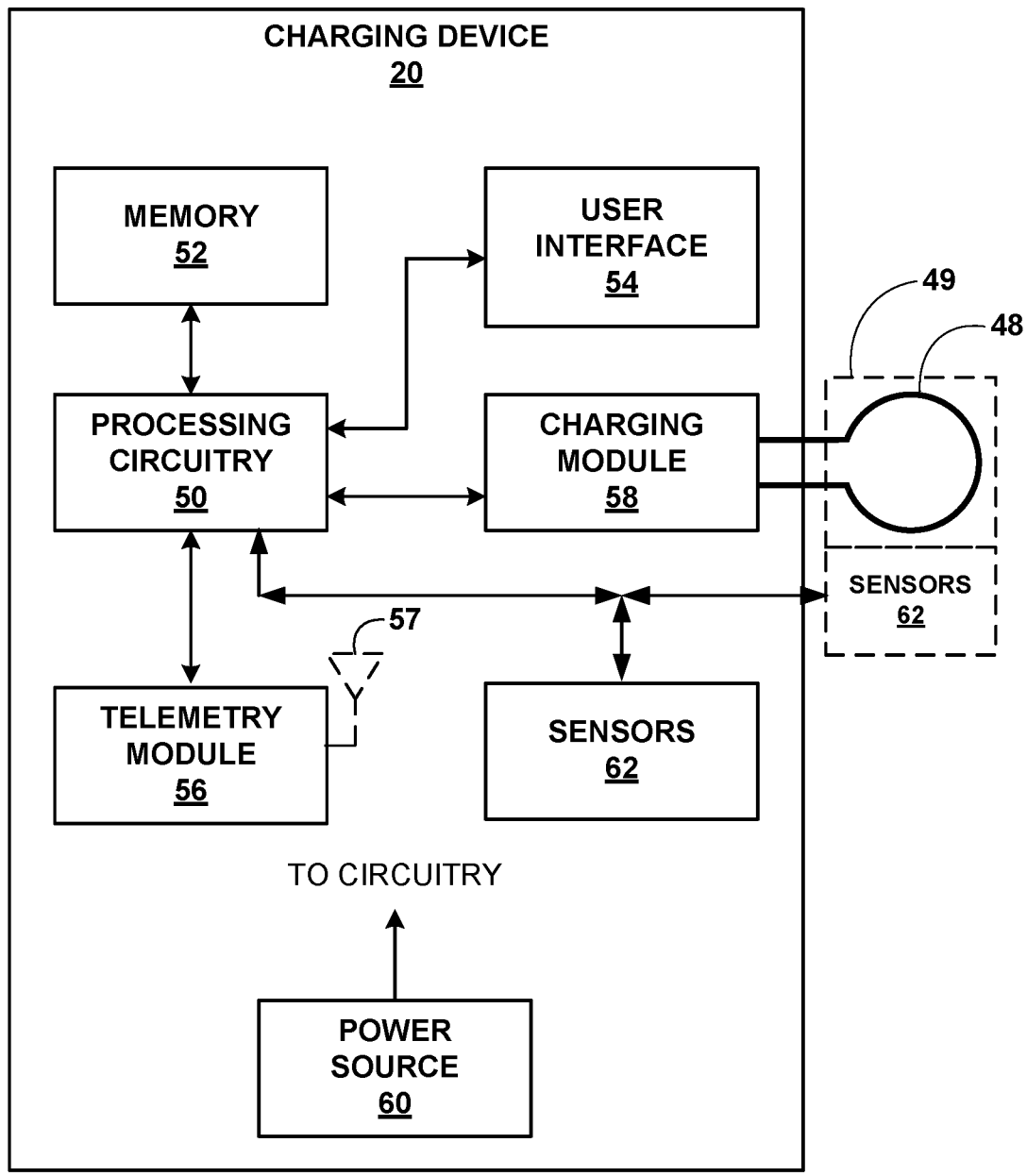
FIG. 3 is a block diagram of the example external charging devices of FIG. 1

As shown in FIG. 2, secondary coil 40 may include a coil of wire or other device capable of inductive coupling with a primary coil disposed external to patient 12, such as primary coil 48 shown in FIG. 3. Although secondary coil 40 is illustrated as a simple loop of in FIG. 2, secondary coil 40 may include multiple turns of wire. In FIG. 2, secondary coil 40 may include a winding of wire configured such that an electrical current can be induced within secondary coil 40 from a magnetic field. The induced electrical current may then be used to recharge rechargeable power source 18. In this manner, the electrical current may be induced in secondary coil 40 associated with rechargeable power source 18. The induction may be caused by electrical current generated in the primary coil of an external device, such as external charging device 20 as shown in FIG. 1, and based on the selected power level. The coupling between secondary coil 40 and the primary coil of external charging device 20 may be dependent upon the alignment of the two coils. Generally, the coupling efficiency increases when the two coils share a common axis and are in close proximity to each other. External charging device 20 and/or IMD 14 may provide one or more audible tones or visual indications of the alignment.

Although inductive coupling is generally described as the method for recharging rechargeable power source 18, other wireless energy transfer techniques may alternatively be used. Any of these techniques may generate heat in IMD 14 such that the charging process can be controlled using the calculated cumulative thermal dose as feedback. In addition, monitored parameters associated with the patient, such as a current posture and/or an activity level associated with the patient having IMD 14 undergoing a recharging process may also be used to control and/or terminate the recharging process that is underway.

Recharge module 38 may include one or more circuits that filter and/or transform the electrical signal induced in secondary coil 40 to an electrical signal capable of recharging the rechargeable power source 18. For example, in alternating current induction, recharge module 38 may include a half-wave rectifier circuit and/or a full-wave rectifier circuit configured to convert alternating current from the induction to a direct current for rechargeable power source 18. The full-wave rectifier circuit may be more efficient at converting the induced energy for rechargeable power source 18. However, a half-wave rectifier circuit may be used to store energy in rechargeable power source 18 at a slower rate. In some examples, recharge module 38 may include both a full-wave rectifier circuit and a half-wave rectifier circuit such that recharge module 38 may switch between each circuit to control the charging rate of rechargeable power source 18 and temperature of IMD 14.

In some examples, recharge module 38 may include a measurement circuit configured to measure the current and/or voltage induced during inductive coupling. This measurement may be used to measure or calculate the power transmitted to IMD 14 from external charging device 20. In some examples, the transmitted power may be used to approximate the temperature of IMD 14 and that of the surrounding tissue. This method may be used to indirectly measure the temperature of tissue in contact with the housing of IMD 14. In other examples, IMD 14 may estimate the transmitted power using the measured voltage or current after recharge module 38 or the charging rate of rechargeable power source 18.

Rechargeable power source 18 may include one or more capacitors, batteries, or other energy storage devices. Rechargeable power source 18 may then deliver operating power to the components of IMD 14. In some examples, rechargeable power source 18 may include a power generation circuit to produce the operating power. Rechargeable power source 18 may be configured to operate through hundreds or thousands of discharge and recharge cycles. Rechargeable power source 18 may also be configured to provide operational power to IMD 14 during the recharge process. In some examples, rechargeable power source 18 may be constructed with materials to reduce the amount of heat generated during charging. In other examples, IMD 14 may be constructed of materials that may help dissipate generated heat at rechargeable power source 18, recharge module 38, and/or secondary coil 40 over a larger surface area of the housing of IMD 14.

Although rechargeable power source 18, recharge module 38, and secondary coil 40 are shown as contained within the housing of IMD 14, at least one of these components may be disposed outside of the housing. For example, secondary coil 40 may be disposed outside of the housing of IMD 14 to facilitate better coupling between secondary coil 40 and the primary coil of external charging device 20. These different configurations of IMD 14 components may allow IMD 14 to be implanted in different anatomical spaces or facilitate better inductive coupling alignment between the primary and secondary coils.

IMD 14 may also include temperature sensor 44. Temperature sensor 44 may include one or more temperature sensors (e.g., thermocouples or thermistors) configured to measure the temperature of IMD 14. Temperature sensor 44 may be disposed internal of the housing of IMD 14, contacting the housing, formed as a part of the housing, or disposed external of the housing. As described herein, temperature sensor 44 may be used to directly measure the temperature of IMD 14 and/or tissue surrounding and/or contacting the housing of IMD 14. Alternatively, temperature sensor 44 may be of a type that need not be thermally coupled to housing to sense the housing temperature. For instance, temperature sensor 44 may be an infrared temperature sensor and/or comprise heat pipes to measure temperature of a portion of IMD 14 to which temperature sensor 44 is not thermally coupled. Processing circuitry 30, or external charging device 20, may use this temperature measurement as the tissue temperature feedback to determine the cumulative thermal dose provided to tissue during charging of rechargeable power source 18. Although a single temperature sensor may be adequate, multiple temperature sensors may provide a better temperature gradient or average temperature of IMD 14. The various temperatures of IMD 14 may also be modeled and provided to determine the cumulative thermal dose. Although processing circuitry 30 may continually measure temperature using temperature sensor 44, processing circuitry 30 may conserve energy by only measuring temperature during recharge sessions. Further, temperature may be sampled at a rate necessary to calculate the cumulative thermal dose, but the sampling rate may be reduced to conserve power as appropriate.

Processing circuitry 30 may also control the exchange of information with external charging device 20 and/or an external programmer using telemetry module 36. Telemetry module 36 may be configured for wireless communication using radio frequency protocols or inductive communication protocols. Telemetry module 36 may include one or more antennas 37 configured to communicate with external device(s), such as external charging device 20 and/or external programmer 24 for example. Communications that are performed by telemetry module 36 may be performed using antenna 37, using secondary coil 40 as an antenna, or using a combination of antenna 37 and secondary coil 40. Processing circuitry 30 may transmit operational information and receive therapy programs or therapy parameter adjustments via telemetry module 36. Also, in some examples, IMD 14 may communicate with other implanted devices, such as stimulators, control devices, or sensors such as sensors 26, via telemetry module 36. Transmission of this information may in some examples be in response to a polling request for the information received from an external device, or may be transmitted for example at some predefined time interval(s), regardless of whether a request for the information has been received. In addition, telemetry module 36 may be configured to transmit the measured tissue temperatures from temperature sensor 44, for example. In some examples, the tissue temperature may be measured adjacent to rechargeable power source 18. In this manner, external charging device 20 may calculate the cumulative thermal dose using the transmitted tissue temperature. In other examples, processing circuitry 30 may calculate the cumulative thermal dose and transmit the calculated cumulative thermal dose using telemetry module 36.

In other examples, processing circuitry 30 may transmit additional information to external charging device 20 related to the operation of rechargeable power source 18. For example, processing circuitry 30 may use telemetry module 36 to transmit indications that rechargeable power source 18 is completely charged, rechargeable power source 18 is fully discharged, or any other charge status (i.e., state-of-charge) of rechargeable power source 18. Processing circuitry 30 may also transmit information to external charging device 20 that indicates any problems or errors with rechargeable power source 18 that may prevent rechargeable power source 18 from providing operational power to the components of IMD 14.

For example, during the recharging process, processing circuitry 30 may monitor signals provided by one or more of the sensors of the activity sensors 46, the sensor circuitry 42, and/or signals provided through the telemetry module 36, and determine a patient status associated with patient 12 at various time intervals throughout the recharge process based on the monitored signals. In various examples, processing circuitry 30 used one or more of these signals to determine a current posture for the patient. The current posture of the patient, in some examples along with additional information, such as patient activity level (e.g., a number, or rate of "footfalls" as determined by the signals from activity sensors 46), may be used by processing circuitry 30 to determine a patient status as either comprising an "active" or an "inactive" status. In some examples, as long as the determined patient status remains as an "active" status, processing circuitry 30 continues to monitor the signals provided by one or more of the sensors of the activity sensors 46, the sensor circuitry 42, and/or signals provided through the telemetry module 36 throughout the recharging process. At some point during the recharging process, processing circuitry 30 may determine that the patient status for patient 12 has changed or transitioned to an "inactive" status. A determination that the patient status has changed from an "active" to an "inactive" in some examples is based on processing circuitry 30 using the received signals from sensors of the activity sensors 46 and/or other sensors to determine a current posture for patient 12, and/or to determine an activity level of patient 12 for some time period prior to the current time.

For example, processing circuitry 30 may determine that, based on the accelerometer signals provided by activity sensors 46 and/or other sensors, a current posture of patient 12 is a posture, such as a lying down posture, that is defined to be a "inactive posture" for patient 12. The indication that the current posture of patient 12 is a "inactive posture" for patient 12 may be based on a prior determination that the current posture detected for patient 12 is a posture pre-defined as a posture that patient 12 may assume when sleeping. The determination that the current posture for patient 12 is a "inactive posture" may then be further analyzed to determine if there has been a minimum level of activity, for example transitions between postures, or movement in general, or that current values for one or more sensed and/or predetermined parameters associated with patient 12 that might indicate that patient 12 is awake based on for example comparison of these sensed parameters to predefined threshold values or pre-defined value ranges. Based on a determination that a minimum level of activity sensed by the sensors of the activity sensors 46 and/or other sensors providing signals to processing circuitry 30 has not occurred during a period of time immediately prior to the current time, processing circuitry 30 may determine that that patient statue is "inactive." As discussed above, a minimum level of activity that may be considered "inactive" may be patient-specific and may be learned by, or programmed into the system. In this manner, a different level of activity may be used as "inactive" for a person that is a restless sleeper as compared to a patient that is a sound sleeper.

The determination of the "inactive" status may indicate that patient 12 is asleep, and based on that indication, processing circuitry 30 may take one or more actions related to the recharging process that is underway. For example, during a recharging process when a patient status is determined to be "inactive," processing circuitry 30 may be configured to generated and to issue, for example through telemetry module 36, an alert signal. The alert signal issued by processing circuitry 30 may be formatted and transmitted through the telemetry module 36 to one or more external devices, such as external charging device 20 shown in FIG. 1. The alert signal may simply include an indication that the "inactive" status has been detected for patient 12. In some examples, the alert signal may include additional information for modifying the recharging process. For example, the alert signal may include instructions to modify the power parameters being used to provide the charging power to the IMD 14 through the primary coil of the external charging device. The instructions may also include instruction to stop the recharging process, e.g. lower the recharging power to a "zero" power level, either temporarily or permanently.

In various examples, processing circuitry 30 is configured to use one or more additional sensed parameter in the process of determining the patient status in addition to the signal(s) provided by the sensors of the activity sensors 46. For example, processing circuitry 30 may receive signals provided by sensing circuitry 42 related to one or more physiological parameters of patient 12, and compare these sensed parameters to threshold values for these parameters that are stored in memory 32, as part of making the determination that the patient status has changed to an "inactive" status. In various examples, the instructions transmitted with respect to modifying the recharging process may be based on one or more of these additional parameters. For example, a state-of-charge associated with the power source 18 may be used by processing circuitry 30 to determine whether to stop the recharging process, or to simply modify the power level being applied to the recharging process.

In some examples, data regarding the temperature of IMD 14 based on signals provided by temperature sensor 44 may be used to determine whether to stop the recharging process, or to modify the power parameter settings being used in the recharging process to recharge power source 18 of IMD 14 when an "inactive" status for patient 12 is detected during a recharging process. Processing circuitry 30 may be configured to generate an "inactive status output signal" in response to detection of a particular current posture of patient 12 along with detection of a particular level of activity for patient 12 during the recharging process. In various examples, processing circuitry 30 is configured to determine a patient status associated with patient 12 at various times throughout the time period when the recharging process is underway. In some examples, a patient status is determined at some pre-defined interval, such as at a 4 Hertz interval.

In response to the "inactive" status output signal described above, in some instances the external charging device providing the electrical energy for the recharging process that is underway is configured to modify one or more parameters associated with the recharging process in order to control the power level being provided to the primary coil for the recharging process. One or more of the recharging parameters, such as the amplitude and/or the duty cycle of the power being applied to the recharging process that may be controlled to lower the power level being provided during a recharging process.

Activity sensors 46 allow IMD 14 to sense the patient posture state, e.g., posture, activity or any other static position or motion of patient 12. In the example of FIG. 2, activity sensors 46 may include one or more posture state sensors, e.g., one or more accelerometers such as three-axis accelerometers, capable of detecting static orientation or vectors in three-dimensions. Example accelerometers may include micro-electro-mechanical accelerometers. In other examples, activity sensors 46 may alternatively or additionally include one or more gyroscopes, pressure transducers or other sensors to sense the posture state of patient 12. Posture state information generated by activity sensors 46 and processing circuitry 30 may correspond to an activity, posture, or posture and activity undertaken by patient 12 or a gross level of physical activity, e.g., activity counts based on footfalls or the like.

Posture state information from activity sensors 46 may be stored in memory 32 to be later reviewed by a clinician, used to adjust therapy, presented as a posture state indication to patient 12, used to determine an activity level of patient 12, or some combination thereof. As an example, processing circuitry 30 may record the posture state parameter value, or output, of the 3-axis accelerometer and assign the posture state parameter value to a certain predefined posture indicated by the posture state parameter value. In some examples, these predefined postures may be defined as "sleep postures" for patient 12, wherein these postures represent postures the patient is likely to assume when the patient is sleeping, or attempting to sleep. In this manner, IMD 14 may be able to track how often patient 12 remains within a certain posture defined within memory 32.

IMD 14 may also store which group or program was being used to deliver therapy when patient 12 was in the sensed posture, and the postures assumed by patient 12 throughout a recharging process performed on rechargeable power source 18. Further, processing circuitry 30 may also adjust therapy for a new posture when activity sensors 46 indicates that patient 12 has in fact changed postures. Therefore, IMD 14 may be configured to provide posture state-responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes. Further, processing circuitry 30 and/or external charging device 20 may be configured to adjust the power level being provided during a recharging process, or to remove the power altogether, based on the determined posture of patient 12, in some examples in conjunction with a determination regarding an activity level associated with the patient.

As described herein, the posture state data, or raw data of the posture state information, is stored by system 10 to be used at a later time. The posture state information may also be used in addition to the therapy adjustment information when the user desires to view more detailed information related to the posture states engaged by patient 12. Memory 32 may store all of the posture state data detected during therapy or use of IMD 14, or memory 32 may periodically offload the posture state data to external charging device 20 and/or external programmer 24, or some other device. In other examples, memory 32 may reserve a portion of the memory to store recent posture state data easily accessible to processing circuitry 30 for analysis. In addition, older posture state data may be compressed within memory 32 to require less memory storage until later needed by external charging device 20 or external programmer 24.

A posture state parameter value from activity sensors 46 that indicates the posture state of patient 12 may constantly vary throughout the daily activities of patient 12. However, a certain activity (e.g., walking, running, or biking) or a posture (e.g., standing, sitting, or lying down) may include multiple posture state parameter values from activity sensors 46. In this manner, a posture state may include a broad range of posture state parameter values. Memory 32 may include definitions for each posture state of patient 12. In one example, the definitions of each posture state may be illustrated as a cone in three-dimensional space. Whenever the posture state parameter value, e.g., a sensed coordinate vector, from the three-axis accelerometer of activity sensors 46 resides within a predefined cone, processing circuitry 30 indicates that patient 12 is in the posture state of the cone. In other examples, posture state parameter value from the 3-axis accelerometer may be compared to a look-up table or equation to determine the posture state in which patient 12 currently resides.

Posture state-responsive stimulation may allow IMD 14 to implement a certain level of automation in therapy adjustments. Automatically adjusting stimulation may free patient 12 from the constant task of manually adjusting therapy parameters each time patient 12 changes posture or starts and stops a certain posture state. Such manual adjustment of stimulation parameters can be tedious, requiring patient 12 to, for example, depress one or more keys of patient programmer 24 multiple times during the patient posture state to maintain adequate symptom control. Alternatively, patient 12 may be unable to manually adjust the therapy if external programmer 24 is unavailable or patient 12 is preoccupied. In some embodiments, patient 12 may eventually be able to enjoy posture state responsive stimulation therapy without the need to continue making changes for different postures via patient programmer 24. Instead, patient 12 may transition immediately or over time to fully automatic adjustments based on posture state. Further, in some examples control and modification of the power level being provided during a recharging process may be automatically controlled and/or adjusted based on the posture and/or activity level detected for a patient during the recharging process.

Although activity sensors 46 is described as containing the 3-axis accelerometer, activity sensors 46 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the patient 12 posture state may be determined from multiple posture state sensors placed at various locations on or within the body of patient 12.

In other embodiments, activity sensors 46 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processing circuitry 30, in some embodiments, to confirm or reject changes in sensed posture state that may result from vibration, patient travel (e.g., in an aircraft, car or train), or some other false positive of posture state. Processing circuitry 30 may process these additional signal output as part of making a determination related to the patient status during a recharging process of rechargeable power source 18.

In some embodiments, processing circuitry 30 may processes the analog output of the posture sensor in activity sensors 46 to determine activity and/or posture data. For example, where the posture sensor comprises an accelerometer, processing circuitry 30 or a processor of activity sensors 46 may process the raw signals provided by the posture sensor to determine activity counts. In some embodiments, processing circuitry 30 may process the signals provided by the posture sensor to determine velocity of motion information along each axis.

In one example, each of the x, y, and z signals provided by the posture sensor has both a DC component and an AC component. The DC components describes the gravitational force exerted upon the sensor and can thereby be used to determine orientation of the sensor within the gravitational field of the earth. Assuming the orientation of the sensor is relatively fixed with respect to the patient, the DC components of the x, y and z signals may be utilized to determine the patient's orientation within the gravitational field, and hence to determine the posture of the patient.

The AC component of the x, y and z signals yields information about patient motion. In particular, the AC component of a signal may be used to derive a value for an activity describing the patient's motion, or activity. This activity may involve a level, direction of motion, or acceleration of the patient.

One method for determining the activity level associated with a patient is an activity count. An activity count may be used to indicate the activity or activity level of patient 12. For example, processing circuitry 30 may sum the magnitudes of the AC portion of an accelerometer signal for N consecutive samples. For instance, assuming sampling occurs as 25 Hz, N may be set to 25, so that count logic provides the sum of the samples that are obtained in one second. This sum may be referred to as an "activity count." The number "N" of consecutive samples may be selected by the processor based on the current posture, if desired. The activity count may be the activity portion of the activity parameter value that is added to the posture portion. The resulting activity parameter value may then incorporate both activity and posture to generate an accurate indication of the motion of patient 12, and/or compared to a threshold level as part of determining the "active" or "inactive" status associated with patient 12 over a particular time period during a recharging process.

As another example, the activity parameter value may be defined describing direction of motion. This activity parameter value may be associated with a vector and an associated tolerance, which may be a distance from the vector. Another example of an activity parameter value relates to acceleration. The value quantifying a level of change of motion over time in a particular direction may be associated with this parameter referenced in the activity parameter value.

Processing circuitry 30 may employ multiple timers that monitor activity level of patient 12, and when a new posture state occurs, as a result of a posture transition. Processing circuitry 30 may use a posture search timer having a search period, where the search timer begins upon the detection of the therapy adjustment and expires when the search period lapses. The posture search timer allows a certain amount of time, or the search period, for patient 12 to finally engage in the intended posture state. In addition, processing circuitry 30 uses a posture stability timer, where the posture stability timer begins upon the sensing of a different posture state and requires a certain amount of time, the stability period, to elapse while patient 12 is in the same posture before the posture can be considered the final posture. A power level adjustment to a recharging process based on posture and/or activity level of a patient in some examples is only associated with a current posture when the current posture is started, i.e., the stability timer is started, prior to the expiration of the search period and the current posture lasts at least as long as the stability period.

Although external charging device 20 and/or external programmer 24 may perform any processing on the posture and activity level information, such as the association of adjusting the power level being provided during a recharging process, processing circuitry 30 of IMD 14 may be configured to analyze the information and generate desired information. For example, processing circuitry 30 may generate nominal or suggested power level changes with respect to the power being applied during a recharging process based upon the current posture, the pre-defined posture information, and/or the values for one or more sensed and/or predetermined parameters compared to threshold information stored in memory 32. In this manner, IMD 14 may transmit the nominal or suggested power level adjustment instructions directly to external charging device 20. Any other shared processing between IMD 14 and external charging device 20 and/or external programmer 24 is also contemplated.

Wireless telemetry in IMD 14 with external charging device 20 and/or external programmer 24, or another device may be accomplished by radio frequency (RF) communication or proximal inductive interaction of IMD 14 with external programmer 24. Telemetry module 36 may send information to and receive information from external charging device 20 and/or external programmer 24 on a continuous basis, at periodic intervals, at non-periodic intervals, or upon request from the external charging device and/or the external programmer. To support RF communication, telemetry module 36 may include appropriate electronic components, such as amplifiers, filters, mixers, encoders, decoders, and the like.

Rechargeable power source 18 delivers operating power to the components of IMD 14. Rechargeable power source 18 may include a small rechargeable or non-rechargeable battery and a power generation circuit to produce the operating power. Recharging may be accomplished through proximal inductive interaction between an external charger and an inductive charging coil within IMD 14. In some examples, power requirements may be small enough to allow IMD 14 to utilize patient motion and implement a kinetic energy-scavenging device to trickle charge a rechargeable battery. In other examples, traditional batteries may be used for a limited period of time. As a further alternative, an external inductive power supply could transcutaneously power IMD 14 when needed or desired.

As mentioned above, IMD 14 collects information relating to whether it is likely that a patient may have fallen asleep during a recharging process. In some examples this information may relate to the quality of sleep experienced by patient 12. Specifically, in some examples IMD 14 monitors one or more physiological parameters of patient 12, and determines values for one or more metrics that indicate the quality of sleep based on values of the physiological parameters. Example physiological parameters that IMD 14 may monitor include activity level, posture, heart rate, respiration rate, respiratory volume, blood pressure, blood oxygen saturation, partial pressure of oxygen within blood, partial pressure of oxygen within cerebrospinal fluid (CSF), muscular activity, core temperature, arterial blood flow, brain wave activity, and the level of melatonin within one or more bodily fluids.

In some external medical device examples of the invention, galvanic skin response may additionally or alternatively be monitored. Further, in some examples, IMD 14 additionally or alternatively monitors the variability of one or more of these parameters. In order to monitor one or more of these parameters, IMD 14 may include or be coupled to one or more sensors such as sensors 26, each of which generates a signal as a function of one or more of these physiological parameters. The detected values of physiological parameters of patient 12, such as activity level, heart rate, respiration rate, respiratory volume, blood pressure, blood oxygen saturation, partial pressure of oxygen within blood, partial pressure of oxygen within cerebrospinal fluid, muscular activity (as detected by electromyogram (EMG), core temperature, arterial blood flow, electroencephalogram (EEG), local field potential (LFP), and galvanic skin response may discernibly change when patient 12 falls asleep or wakes up. In particular, these physiological parameters may be at different, in and in some cases lower values when patient 12 is asleep. Further, the variability of at least some of these parameters, such as heart rate and respiration rate, may be at a low value when the patient is asleep.

Processing circuitry 30 may also determine when patient 12 is likely to be asleep, e.g., identify the times that patient 12 falls asleep and wakes up, in order to determine one or more sleep quality metric values. The sleep quality metric values may be used in conjunction with a determination of a current posture of patient 12 and/or in combination with one or more other sensed and/or predetermined parameters to determine a status, for example "active" or "inactive" status, associated with a patient at some point during a recharging process being undertaken by the patient.

FIG. 3 is a block diagram of the example external charging devices of FIG. 1. While external charging device 20 as illustrated in FIG. 3 may generally be described as a hand-held device, external charging device 20 may be a larger portable device or a more stationary device. In addition, in other examples, external charging device 20 may be included as part of an external programmer or include functionality of an external programmer. In addition, external charging device 20 may be configured to communicate with an external programmer, such as external programmer 24 shown in FIG. 1. As illustrated in FIG. 3, external charging device 20 may include a processing circuitry 50, memory 52, user interface 54, telemetry module 56, charging module 58, coil 48, and power source 60. In various examples, coil 48 is referred to as the "primary coil" of a recharging device in a recharging system. In some examples, coil 48 is enclosed in a pad 49, similar to the energy transfer device 23 shown in FIG. 1.

Referring again to FIG. 3, memory 52 may store instructions that, when executed by processing circuitry 50, cause processing circuitry 50 and external charging device 20 to provide the functionality ascribed to external charging device 20 throughout this disclosure. In general, external charging device 20 comprises any suitable arrangement of hardware, alone or in combination with software and/or firmware, to perform the techniques attributed to external charging device 20, and processing circuitry 50, user interface 54, telemetry module 56, and charging module 58. In various examples, external charging device 20 may include one or more processors, such as one or more microprocessors, DSPs, ASICs, FPGAs, or any other equivalent integrated or discrete logic circuitry, as well as any combinations of such components.

External charging device 20 also, in various examples, may include a memory 52, such as RAM, ROM, PROM, EPROM, EEPROM, flash memory, a hard disk, a CD-ROM, comprising executable instructions for causing the one or more processors to perform the actions attributed to them. Moreover, although processing circuitry 50, telemetry module 56, and charging module 58 are described as separate modules, in some examples, processing circuitry 50 and telemetry module 56 are functionally integrated. In some examples, processing circuitry 50 and telemetry module 56 and charging module 58 correspond to individual hardware units, such as ASICs, DSPs, FPGAs, or other hardware units.

Memory 52 may include instructions that cause processing circuitry 50 to calculate cumulative thermal doses, establish thresholds, select power levels based on the cumulative thermal doses and otherwise control charging module 58, communicate with IMD 14, or instructions for any other functionality. In addition, memory 52 may include a record of selected power levels, calculated cumulative thermal doses, or any other data related to recharging the rechargeable power source 18. Processing circuitry 50 may, when requested, transmit any of this stored data in memory 52 to another computing device for review or further processing.

In some examples, memory 52 may be configured to store data representative of a tissue model used by processing circuitry 50 to calculate the tissue temperature based on the tissue model and power transmitted to rechargeable power source 18 over a period of time. The tissue model may indicate how temperate of tissue surrounding IMD 14 changes over time based on, e.g., as a function of power received from primary coil 48. Therefore, processing circuitry 50 may be able to estimate the tissue temperature without direct measurement of the temperature of tissue surrounding the housing of IMD 14.

In some examples, memory 52 may include stored information, such as postures defined as "inactive postures" for a patient, that when accessed by processing circuitry 50 allow processing circuitry 50 to determine if a current posture of the patient is a posture defined as a "inactive posture" for the patient. In addition, memory 52 may store one or more threshold values that, when accessed by processing circuitry 50, allow processing circuitry 50 to determine a current status, such as "active" or "inactive" status, for the patient based on comparing sensed and predetermined parameters associated with the patient to the threshold values stored in memory 52. In various examples, based on the current posture and/or an activity level determined for a given patient during a recharging process, processing circuitry 50 is configured to further control the power level(s) being applied to the recharging process, including lowering or completely removing the power being applied by charging module 58 to primary coil 48 based on the posture/activity level determinations.

In various examples, memory 52 includes stored values for recharging parameters associated with different power levels that may be used during a recharging process. For example, memory 52 may include stored values for amplitudes, pulse widths and duty cycles, and other parameters, such as a waveform, that may be applied as the different power levels provided to a recharging process. In various examples, processing circuitry 50 may access these values stored in memory 52 to configure charging module 58 to provide a power level at primary coil 48 consistent with a predefined power level setting.

The determination as to which power level setting is to be applied at any given time during a recharging process being performed by external charging device 20 may be determine by instructions sent to external charging device 20 through telemetry module 56, for example from IMD 14, or for example based on user inputs provided through user interface 54. In various examples, processing circuitry 50 is configured to receive, for example through telemetry module 56, one or more signals provided by other devices, such as IMD 14 and/or sensors 26, and to process these signals to determine the proper power level setting for the power being provided to primary coil 48 during a recharging process. Processing circuitry may be configured in various examples to perform any of the processing of sensor signals and/or additional parameters to determine the patient status, and or to control the power level(s) applied to a recharging process based on the patient status as described with respect to processing circuitry 30 of IMD 14. In various examples one or more signals provided to external charging device 20 by other devices may include information and/or data related to a current posture, one or more sensed or predetermined parameters associated with patient 12, and/or other information such as a state of charge of rechargeable power source 18, and/or temperature(s) related to the IMD and/or other parameters related to the power provided to primary coil 48 as part of the recharging process. In some examples, external charging device 20 is configured to transmit, using telemetry module 56, a polling request comprising a request for another device, such as IMD 14 and/or sensors included in the system, to forward data to the external charging device in response to the polling request. In some examples, external charging device is configured to receive data, for example data transmitted from the sensors and/or IMD 14, that is transmitted at some time interval(s), without the need for external charging device 20 to issues a request, e.g., to poll for the data.

User interface 54 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processing circuitry 50 may present and receive information relating to the charging of rechargeable power source 18 of IMD 14 via user interface 54. For example, user interface 54 may indicate when charging is occurring, quality of the alignment between coils 40 and 48, the selected power level, current charge level of rechargeable power source 18, duration of the current recharge session, anticipated remaining time of the charging session, or any other information. Processing circuitry 50 may receive some of the information displayed on user interface 54 from IMD 14 in some examples. In some examples, user interface 54 may provide a prompt, for example a visually displayed prompt, a tactile prompt (such as a vibration), and/or an audio prompt, to alert the patient that the "inactive" status has been detected, and to request a patient input indicating that the patient for example is awake. If no such response is received in reply to such a prompt, processing circuitry 50 may determine that the patient is likely asleep, and may then further control the recharging process, for example by lowering or completely removing the power being applied to primary coil 48, as a result of not receiving a reply to the prompt from the patient.

User interface 54 may also receive user input via user interface 54. The input may be, for example, in the form of pressing a button on a keypad or selecting an icon from a touch screen. The input may request starting or stopping a recharge session, a desired level of charging, or one or more statistics related to charging rechargeable power source 18 (e.g., the cumulative thermal dose). In this manner, user interface 54 may allow the user to view information related to the charging of rechargeable power source 18 and/or receive charging commands. This input may also be used to provide the mechanism for the patient responding to the prompt described above issued when processing circuitry 50 has determined that the patient status has changed to "inactive" and requesting that the patient reply to confirm that the patient is in fact awake. Further, an indication that inputs to the user interface are being received and that would be provided as a result of inputs made by the patient, may indicate an activity level, and thus may be considered as an indication that the patient is awake. Indications of these patient inputs may be transmitted to IMD 14 by external charging device 20, for further processing by IMD 14 to determine, or for example to confirm, that the activity level of the patient at the time the inputs are receive corresponds to an "active" status for the patient.

As described above, external charging device 20 also includes components to transmit power to recharge rechargeable power source 18 associated with IMD 14. As shown in FIG. 3, external charging device 20 includes primary coil 48 and charging module 58 coupled to power source 60. Charging module 58 may be configured to generate an electrical current in primary coil 48 from voltage stored in power source 60. Although primary coil 48 is illustrated as a simple loop in FIG. 3, primary coil 48 may include multiple turns of wire. Charging module 58 may generate the electrical current according to a power level selected by processing circuitry 50 based on the cumulative thermal dose. As described herein, processing circuitry 50 may select a "high" power level, a "medium" power level, or a "low" power level, or a variety of different power levels to control the rate of recharge in rechargeable power source 18 and the temperature of IMD 14. In some examples, processing circuitry 50 may control charging module 58 based on a power level selected by processing circuitry 30 of IMD 14.

Primary coil 48 may include a coil of wire, e.g., having multiple turns, or other device capable of inductive coupling with a secondary coil 40 disposed within patient 12. Primary coil 48 may include a winding of wire configured such that an electrical current generated within primary coil 48 can produce a magnetic field configured to induce an electrical current within secondary coil 40. The induced electrical current may then be used to recharge rechargeable power source 18. In this manner, the electrical current may be induced in secondary coil 40 associated with rechargeable power source 18. The coupling efficiency between secondary coil 40 and primary coil 48 of external charging device 20 may be dependent upon the alignment of the two coils. Generally, the coupling efficiency increases when the two coils share a common axis and are in close proximity to each other. User interface 54 of external charging device 20 may provide one or more audible tones or visual indications of the alignment.

Charging module 58 may include one or more circuits that generate an electrical signal, and an electrical current, within primary coil 48. Charging module 58 may generate an alternating current of specified amplitude and frequency in some examples. In other examples, charging module 58 may generate a direct current. In any case, charging module 58 may be capable of generating electrical signals, and subsequent magnetic fields, to transmit various levels of power to IMD 14. In this manner charging module 58 may be configured to charge rechargeable power source 18 of IMD 14 with the selected power level.

The power level that charging module 58 selects for charging may be used to vary one or more parameters of the electrical signal generated for coil 48. For example, the selected power level may specify a wattage, electrical current of primary coil 48 or secondary coil 40, current amplitude, voltage amplitude, duty cycle, or any other parameter that may be used to modulate the power transmitted from coil 48. In this manner, each power level may include a specific parameter set that specifies the signal for each power level. Changing from one power level to another power level, e.g., a "high" power level to "medium" or a "low" power level, may include adjusting one or more parameters. The parameters of each power level may be selected based on hardware characteristics of external charging device 20 and/or IMD 14.

Power source 60 may deliver operating power to the components of external charging device 20. Power source 60 may also deliver the operating power to drive primary coil 48 during the charging process. Power source 60 may include a battery and a power generation circuit to produce the operating power. In some examples, the battery may be rechargeable to allow extended portable operation. In other examples, power source 60 may draw power from a wired voltage source such as a consumer or commercial power outlet.

Although power source 60 and charging module 58 are shown within a housing of external charging device 20 and primary coil 48 is shown external to external charging device 20, different configurations may also be used. For example, primary coil 48 may also be disposed within the housing of external charging device 20. In another example, power source 60, charging module 58, and primary coil 48 may be all located external to the housing of external charging device 20 and coupled to external charging device 20.

In some examples, external charging device 20 may have one or more sensors 62, such as one or more temperature sensors and/or one or more sensors for determining posture and/or activity. In some examples, one or more of sensors 62 are located within a housing of the external charging device 20. In some examples, one or more of sensors 62 may be located outside the housing, for example adjacent to coil 48 and/or enclosed in pad 49. The signals provided by sensors 62, for example sensed values related to temperature, posture, and/or activity, may be used in conjunction with one or more such sensors located elsewhere, such as in IMD 14, to determine patient status, as discussed further below.

Telemetry module 56 supports wireless communication between IMD 14 and external charging device 20 under the control of processing circuitry 50. Telemetry module 56 may also be configured to communicate with another computing device via wireless communication techniques, or direct communication through a wired connection. Telemetry module 56 may also be configured to communicate directly with one or more sensors, such as sensors 26, for example to receive output signals from these sensors without going through IMD 14. In some examples, telemetry module 56 may be substantially similar to telemetry module 36 of IMD 14 described herein, providing wireless communication via an RF or proximal inductive medium. In some examples, telemetry module 56 may include a separate antenna 57, which may take on a variety of forms, such as an internal or external antenna.

Examples of local wireless communication techniques that may be employed to facilitate communication between external charging device 20 and IMD 14, sensors 26, and/or other computing devices include RF communication according to the 802.11 or Bluetooth specification sets, or other standard or proprietary telemetry protocols. In this manner, other external devices may be capable of communicating with external charging device 20 without needing to establish a secure wireless connection. As described herein, telemetry module 56 may be configured to receive a measured tissue temperature from IMD 14. The tissue temperature may be measured adjacent to rechargeable power source 18, such as near the housing of IMD 14 or external of the housing. Although IMD 14 may measure the tissue temperature, one or more different implantable temperature sensors (e.g., standalone implantable temperature sensing devices) may independently measure the tissue temperature at different positions and transmit the temperature to external charging device 20. In some examples, multiple temperature readings by IMD 14 may be averaged or otherwise used to produce a single temperature value that is transmitted to external charging device 20. The temperature may be sampled and/or transmitted at different rates, e.g., on the order of microseconds, milliseconds, seconds, minutes, or even hours. Processing circuitry 50 may then use the received tissue temperature to calculate the cumulative thermal dose.

Alternatively or additionally, external charging device 20 may receive one or more temperature readings from one or more temperature sensors 62 carried by external charging device 20. These temperature readings may be used separately or in combination with those temperature readings received via telemetry module 56 from IMD 14 or other implantable sensors to determine heating associated with recharge. For example, these additional sensors may provide an indication of heating occurring at a surface of a patient, such as at the skin surface.

In various examples, external charging device 20 may receive sensor information from IMD 14 and/or sensors 26, and based on these received signals, processing circuitry 50 may further process the signal(s) to determine the status of a patient, such as an "active" or an "inactive" status, by performing any of the functions descried as being performed by processing circuitry 30 of IMD 14 with regards to determining patient status during a recharging process. In various examples, the determination of the patient status is performed by a combination of processing performed by both processing circuitry 30 of IMD 14 and processing circuitry 50 of external charging device 20.

Figure 4:
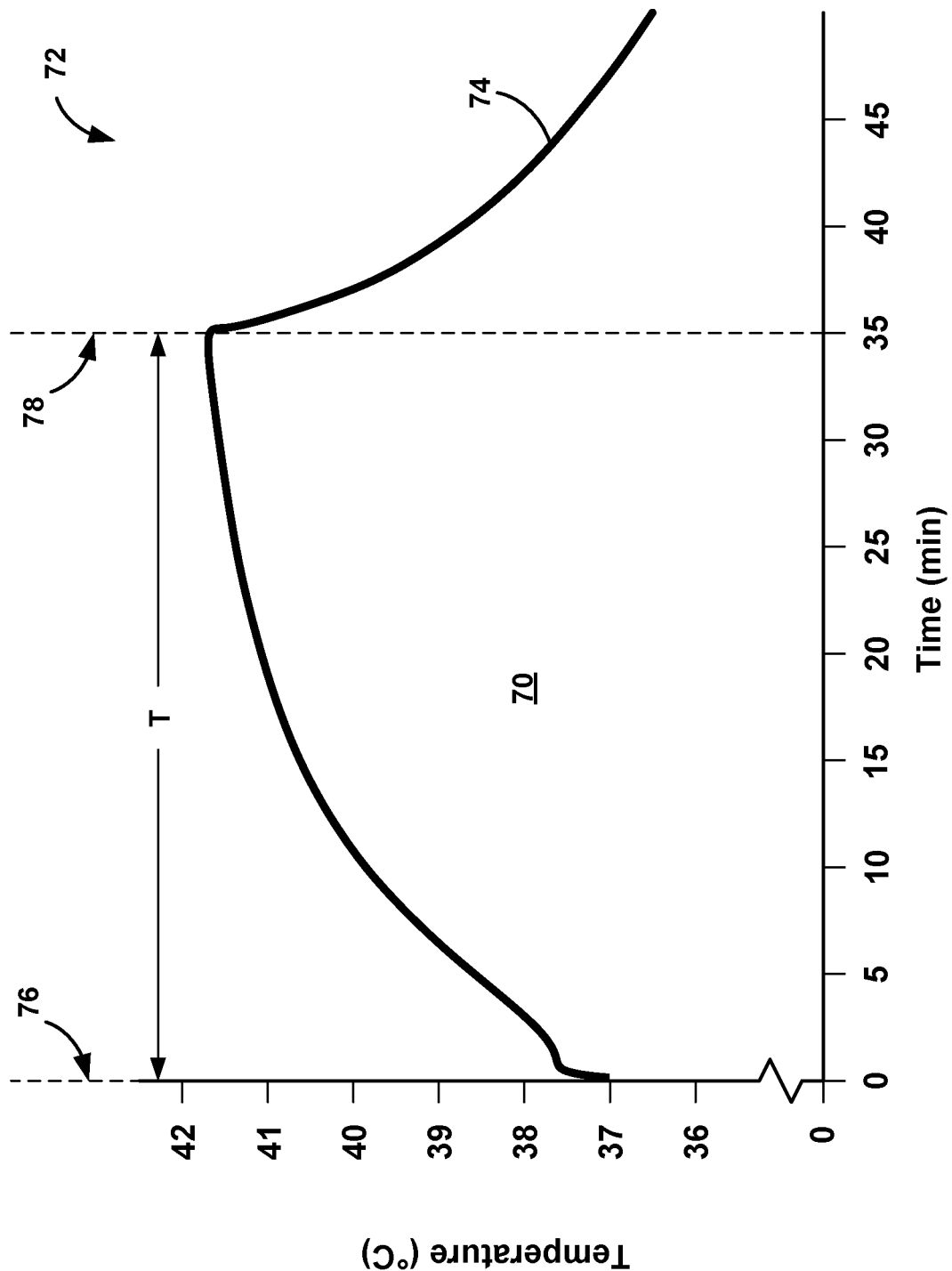
FIG. 4 is a graph of example temperatures generated in a patient during IMD recharging over a period of time.

FIG. 4 is a graph 72 of example temperatures generated in a patient during IMD recharging over a period of time. As shown in FIG. 4, graph 72 includes temperature 74 over time during recharging of a rechargeable power source, such as rechargeable power source 18. The temperature 74 may be measured within IMD 14, on the housing of IMD 14, within external charging device 20, within tissue near or at a cutaneous boundary, or within tissue surrounding IMD 14. Alternatively, the temperature may be calculated based on power transmitted to IMD 14 and a tissue model of how tissue would respond based on the power transmitted over time. Therefore, temperature 74 may be representative of how temperatures in tissue surrounding and/or contacting the housing of IMD 14 may change when rechargeable power source 18 is being recharged with given levels of recharge power.

Graph 72 may indicate how temperature 74 changes when external charging device 20 initially selects a "high" power level for charging, and changes to a low power level once the cumulative thermal dose has been reached. Once charging of rechargeable power source 18 begins at the zero-minute mark (power level change 76), temperature 74 begins to increase from approximately 37 degrees Celsius. Because external charging device 20 transmits power at a "high" power level, rechargeable power source 18 may charge at a fast rate and the temperature of IMD 14 and surrounding tissue may increase at a relatively higher rate as compared to slower charging rates with lower transmitted power levels. Temperature 74 may level out at a certain magnitude based on the transmitted power and the ability of the tissue to dissipate heat.

Time T may indicate the amount of time that it takes for the cumulative thermal dose to reach the thermal dose threshold. The cumulative thermal dose may be determined to be representative of the total amount of heat the tissue has been exposed to over a period of time. The cumulative thermal dose may be calculated using a variety of different techniques that indicate this total amount of heat. For example, temperature 74 may be integrated over time to calculate the cumulative thermal dose in degree-minutes.

Cumulative thermal dose 70, e.g., the area under the curve of temperature 74, would thus be representative of the total amount of heat delivered to tissue from IMD 14 over time. Since the normal physiological temperature of tissue is approximately 37 degrees Celsius, temperature 74 may only be integrated for temperatures about this 37 degree Celsius floor. However, the cumulative thermal dose may be calculated using any temperature as a floor as long as the thermal dose threshold, or any other thresholds, are established using this floor temperature as well.

In other examples, the cumulative thermal dose may be calculated using alternative techniques. For example, external charging device 20 may average temperature 74 for each segment of time (e.g., each minute) and sum the average temperatures for each minute to calculate the cumulative thermal dose. Alternatively, the cumulative thermal dose may be calculated using more complex equations that may account for the effect to tissue at different magnitude of temperatures, e.g., weight time differently at different temperatures. As temperature 74 increases, the effects of each incremental change in temperature may cause a disproportional increase in undesirable tissue effects and decrease patient comfort. In other words, each degree change may exponentially decrease the amount of time tissue can safely be exposed to that temperature. For example, it may be safe to expose tissue to 41 degrees Celsius for 4 hours, but a small increase in temperature to 43 degrees may decrease the safe exposure time to only 30 minutes. In this manner, the cumulative thermal dose may be calculated to account for the non-linear relationship between temperature and undesirable side effects over time.

Once the cumulative thermal dose exceeds the thermal dose threshold, external charging device 20 may decrease the charging power to a low power level at power level change 78. In the example of FIG. 4, the cumulative thermal dose exceeded the thermal dose threshold at approximately 35 minutes after beginning to charge rechargeable power source 18 with the "high" power level. The "low" power level may thus decrease the rate that rechargeable power source 18 is charged and temperature 74 may decrease with this decreased transmitted power. In other examples, external charging device 20 may select the "low" power level before the thermal dose threshold is reached and terminate charging once the thermal dose threshold is reached. In any case, external charging device 20 may select the power level for charging rechargeable power source 18 based on the cumulative thermal dose calculated using temperature 74.

Temperature 74 of graph 72 is only an example of tissue temperature changes due to charging rechargeable power source 18 in IMD 14. In the example of FIG. 4, temperature 74 may increase to approximately 41.5 degrees Celsius prior to reducing the power level for charging. In other examples, temperature 74 may change at faster or slower rates. In addition, temperature 74 may plateau at lower temperatures, plateau at higher temperatures, or not plateau at all during the recharge session. In some examples, temperature 74 may reach temperatures in excess of 42 degrees Celsius or even 43 degrees Celsius. In this manner, the thermal dose threshold, method of calculating the cumulative thermal dose, and other variables for managing the cumulative thermal dose received by patient 12 may be adjusted based on the specific characteristics of external charging device 20, IMD 14, and even patient 12.

However, graph 72 may represent the expected temperature behavior curve based on for example tissue models, but may not include calculations concerning certain end user conditions, such as circumstance wherein the primary coil of a recharging system is located between a patient and some other object, such as a mattress or a cushion, that might not allow for normal ambient temperature cooling of the primary coil during the recharging process. As such, the systems, devices, and methods described herein provide a further safety measure for the patient by monitoring posture and activity levels of the patient during the recharging process, and in some examples to automatically control the recharging process to assure the temperatures associated with the recharging process do not reach any unexpected or unsafe levels, even if the patient may have fallen asleep on the device including the primary coil during the recharging process. In various examples, detection that that patient may have fallen asleep during the recharging process may be based on a determination of a current posture and/or activity level for the patient. The devices and techniques that may be used for determining a posture and/or activity levels associated with a patient are described in further detail throughout this disclosure.

Figure 5A:
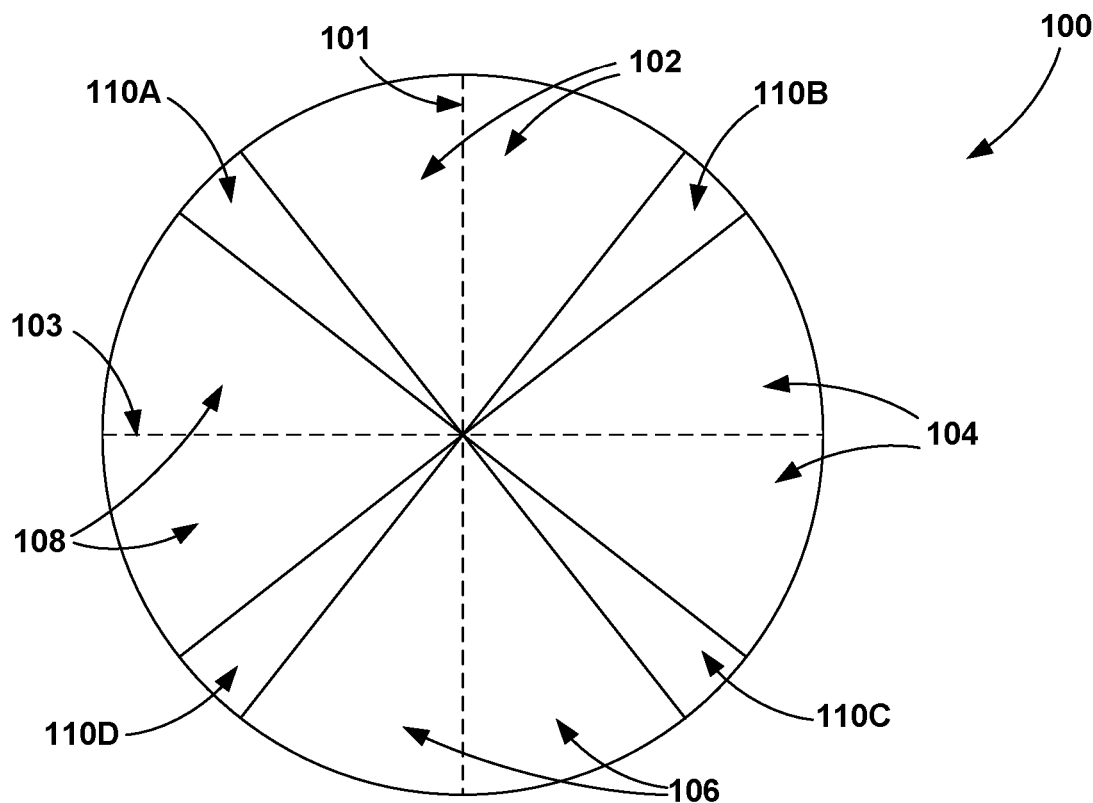
FIGS. 5A-5C are conceptual illustrations of posture cones that may be used to define a posture state of a patient based on signals sensed by a posture state sensor or other sensors in accordance with the techniques described in this disclosure.
Figure 5B:
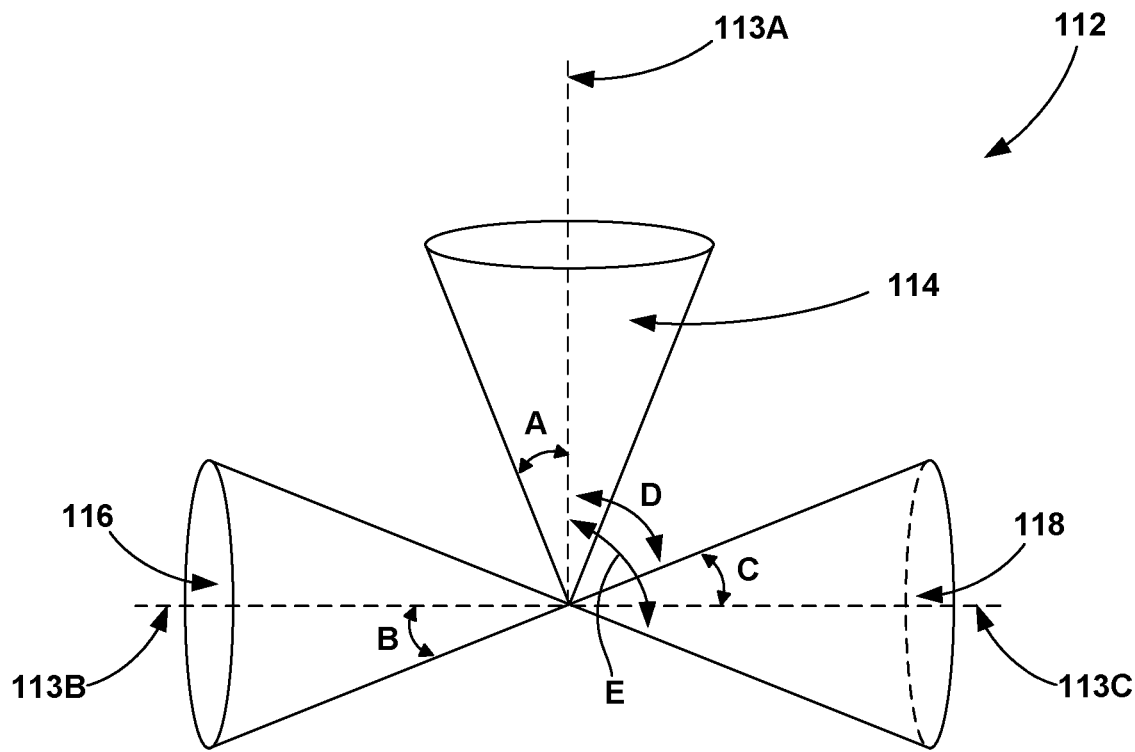
Figure 5C:
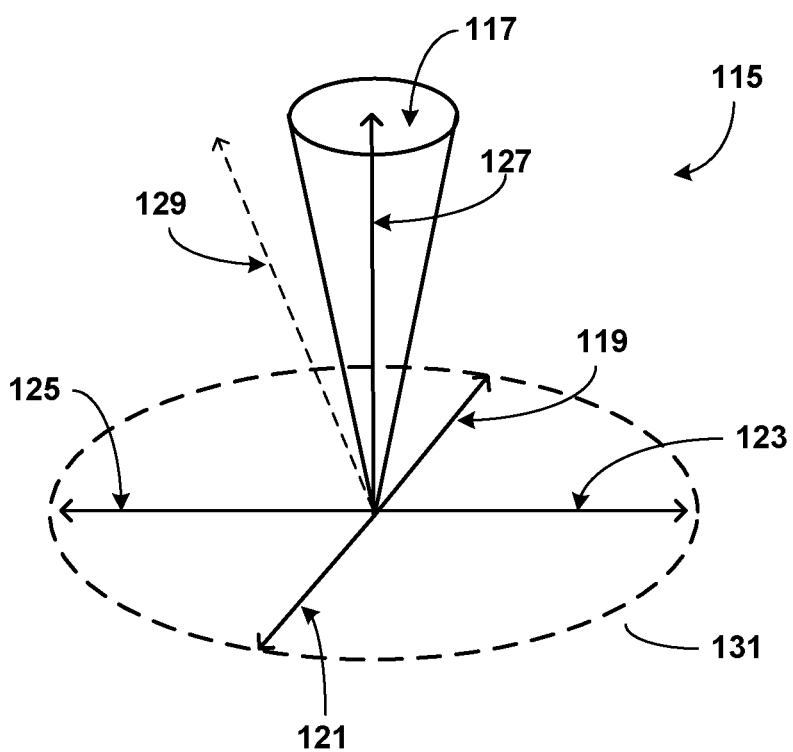

FIGS. 5A-5C are conceptual illustrations of postures state spaces 100, 112, 115 within which posture reference data may define the postures, including a current posture, of patient 12. Posture reference data may define certain regions associated with particular posture states of patient 12 within the respective postures spaces 100, 112, 115. The output of one or more posture state sensors may be analyzed by activity sensors 46 as shown in FIG. 3 with respect to posture state spaces 100, 112, 115 as shown in FIGS. 5A-5C to determine a current posture state of patient 12. For example, if the output of one or more posture state sensors is within a particular posture region defined by posture state reference data, activity sensors 46 may determine that patient 12 is within the posture state associated with the respective posture state region.

In some cases, one or more posture state regions may be defined as posture state cones. Posture state cones may be used to define a posture state of patient 12 based on the output from a posture state sensor of a posture state according to an example method for posture state detection. A posture state cone may be centered about a posture state reference coordinate vector that corresponds to a particular posture state. In the examples of FIGS. 5A and 5B, the activity sensors 46 of IMD 14 may use a posture state sensor, e.g., a three-axis accelerometer that provides data indicating the posture state of patient 12, to sense posture vectors.

While the sensed data may be indicative of any posture, postures of patient 12 will generally be used below to illustrate the concept of posture cones. As shown in FIG. 5A, posture state space 100 represents a vertical plane dividing patient 12 from left and right sides, or the sagittal plane. A posture state parameter value from two axes of the posture state sensor may be used to determine the current posture state of patient 12 according to the posture state space 100. The posture state data may include x, y and z coordinate values.

A posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle or distance of the reference coordinate vector, or if the sensed posture state vector and the reference coordinate vector produce a cosine value in a specified cosine range, then posture state vector is determined to reside within the posture cone defined by the reference coordinate vector.

Posture space 100 is segmented into different posture cones that are indicative of a certain posture state of patient 12. In the example of FIG. 5A, upright cone 102 indicates that patient 12 is sitting or standing upright, lying back cone 108 indicates that patient 12 is lying back down, lying front cone 104 indicates that patient 12 is lying chest down, and inverted cone 106 indicates that patient 12 is in an inverted position. Other cones may be provided, e.g., to indicate that patient 12 is lying on the right side or left side. For example, a lying right posture cone and a lying left posture cone may be positioned outside of the sagittal plane illustrated in FIG. 5A. In particular, the lying right and lying left posture cones may be positioned in a coronal plane substantially perpendicular to the sagittal plane illustrated in FIG. 5A. For ease of illustration, lying right and lying left cones are not shown in FIG. 5A.

Vertical axis 101 and horizontal axis 103 are provided for orientation of posture state area 100, and are shown as orthogonal for purposes of illustration. However, posture cones may have respective posture reference coordinate vectors that are not orthogonal in some cases. For example, individual reference coordinate vectors for cones 102 and 106 may not share the same axis, and reference coordinate vectors for cones 104 and 108 may not share the same axis. Also, reference coordinate vectors for cones 104 and 108 may or may not be orthogonal to reference coordinates vectors for cones 102, 106. Moreover, the reference coordinate vectors need not reside in the same plane. Therefore, although orthogonal axes are shown in FIG. 5A for purposes of illustration, respective posture cones may be defined by individualized reference coordinate vectors for the cones.

IMD 14 may monitor the posture state parameter value of the posture state sensor to produce a sensed coordinate vector and identify the current posture of patient 12 by identifying which cone the sensed coordinated vector of the activity sensors 46 resides. For example, if the posture state parameter value corresponds to a sensed coordinate vector that falls within lying front cone 104, IMD 14 determines that patient 12 is lying down on their chest. IMD 14 may store this posture information as a determined posture state or as raw output from the posture state sensor, change therapy according to the posture, or both. Additionally, IMD 14 may communicate the posture information to external charging device 20 and/or to patient programmer 24 so that the external charging device and/or the patient programmer can present a posture state indication to patient 12.

In addition, posture state area 100 may include hysteresis zones 110A, 110B, 110C, and 110D (collectively "hysteresis zones 110"). Hysteresis zones 110 are positions within posture state area 100 where no posture cones have been defined. Hysteresis zones 110 may be particularly useful when IMD 14 utilizes the posture state information and posture cones to adjust therapy automatically. If the posture state sensor indicates that patient 12 is in upright cone 102, IMD 14 would not detect that patient 12 has entered a new posture cone until the posture state parameter value indicates a different posture cone. For example, if IMD 14 determines that patient 12 moves to within hysteresis zone 110A from upright cone 102, IMD 14 retains the posture as upright. In this manner, IMD 14 does not change the corresponding therapy until patient 12 fully enters a different posture cone. Hysteresis zones 110 prevent IMD 14 from continually oscillating between different therapies when patient 12's posture state resides near a posture cone boundary.

Each posture cone 102, 104, 106, 108 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state. The reference coordinate vector may be defined based on posture sensor data generated by a posture state sensor while patient 12 occupies a particular posture state desired to be defined using the reference coordinate vector. For example, a patient may be asked to occupy a posture so that a reference coordinate vector can be sensed for the respective posture. In this manner, vertical axis 101 may be specified according to the patient's actual orientation. Then, a posture cone can be defined using the reference coordinate vector as the center of the cone.

Vertical axis 101 in FIG. 5A may correspond to a reference coordinate vector sensed while the patient was occupying an upright posture state. Similarly, a horizontal axis 103 may correspond to a reference coordinate vector sensed while the patient is occupying a lying posture state. A posture cone may be defined with respect to the reference coordinate vector. Although a single axis is shown extending through the upright and inverted cones 102, 106, and another single axis is shown extending through the lying down and lying up cones 104, 108, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 102 may have an angle of eighty degrees, +40 degrees to −40 degrees from the positive vertical axis 101. In some cases, lying cones may be defined relative to the reference coordinate vector of the upright cone 102. For example, lying up cone 108 may have an angle of eighty degrees, −50 degrees to −130 degrees from the positive vertical axis 101. Inverted cone 106 may have an angle of eighty degrees, −140 degrees to +140 degrees from vertical axis 101. In addition, lying down cone 104 may have an angle of eighty degrees, +50 degrees to +130 degrees from the positive vertical axis 101. In other examples, each posture cone may have varying angle definitions, and the angles may change during therapy delivery to achieve the most effective therapy for patient 12.

Alternatively or additionally, instead of an angle, posture cones 102, 104, 106, 108 may be defined by a cosine value or range of cosine values in relation to vertical axis 101, horizontal axis 103, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture state sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 102, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 104, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 104 may be defined with reference to the upright cone 102, such that the cosine range may extend between a maximum and minimum values determined relative to the reference coordinate vector for the upright cone.

In other examples, posture state area 100 may include additional posture cones than those shown in FIG. 5A. For example, a reclining cone may be located between upright cone 102 and lying back cone 108 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 102), lying back posture (e.g., within lying back cone 108), and a reclining back posture. Thus, a posture cone that defines the reclining back posture may be useful for providing efficacious posture-responsive therapy to patient 12. In other examples, posture state area 100 may include fewer posture cones than cones 102, 104, 106, 108 shown in FIG. 5A. For example, inverted cone 106 may be replaced by a larger lying back cone 108 and lying front cone 104. In various examples, any of cones 102, 104, 106, and 108, and any intermediate cones as described above, may be designed as "inactive posture" for a specific patient 12. These postures may be pre-defined to represent postures the patient 12 may assume when sleeping. This information, along with other information such as an activity level, in various examples is used to control the power level being applied during a recharging process of a rechargeable power source of a IMD implanted within the patient.

FIG. 5B illustrates an example posture state space 112 that is a three-dimensional space in which the posture state parameter value from the posture state sensor is placed in relation to the posture cones. Posture state space 112 is substantially similar to posture state area 100 of FIG. 5A. However, the posture state parameter value derived from all three axes of a 3-axis accelerometer may be used to accurately determine the posture state of patient 12. In the example of FIG. 5B, posture state space 112 includes upright cone 114, lying back cone 116, and lying front cone 118. Posture state space 112 also includes hysteresis zones (not shown) similar to those of posture state area 100. In the example of FIG. 5B, the hysteresis zones are the spaces not occupied by a posture cone, e.g., upright cone 114, lying back cone 116, and lying front cone 118.

Posture cones 114, 116 and 118 also are defined by a respective center line 113A, 113B, or 113C, and associated cone angle A, B, or C. For example, upright cone 114 is defined by center line 113A that runs through the center of upright cone 114. Center line 113A may correspond to an axis of the posture state sensor or some other calibrated vector. In some embodiments, each center line 113A, 113B, 113C may correspond to a posture reference coordinate vectors defined for the respective postures, e.g., the upright posture. For instance, assuming that patient 12 is standing, the DC portion of the x, y, and z signals detected by the posture state sensor of activity sensors 46 define a posture vector that corresponds to center line 113A. The x, y, and z signals may be measured while patient 12 is known to be in a specified position, e.g., standing, and the measured vector may be correlated with the upright posture state. Thereafter, when the DC portions of the posture state sensor signal are within some predetermined cone tolerance or proximity, e.g., as defined by an angle, distance or cosine value, of the posture reference coordinate vector (i.e., center line 113A), it may be determined that patient 12 is in the upright posture. In this manner, a sensed posture coordinate vector may be initially measured based on the output of one or more posture state sensors of activity sensors 46, associated with a posture state, such as upright, as a reference coordinate vector, and then later used to detect a patient's posture state.

As previously indicated, it may be desirable to allow some tolerance to be associated with a defined posture state, thereby defining a posture cone or other volume. For instance, in regard to the upright posture state, it may be desirable to determine that a patient who is upright but leaning slightly is still in the same upright posture state. Thus, the definition of a posture state may generally include not only a posture reference coordinate vector (e.g., center line 113A), but also a specified tolerance. One way to specify a tolerance is by providing an angle, such as cone angle A, relative to coordinate reference vector 113A, which results in posture cone 114 as described herein. Cone angle A is the deflection angle, or radius, of upright cone 114. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 5B, cone angles A, B, and C are approximately 20 degrees. Cone angles A, B, and C may be different, and center lines 113A, 113B, and 113C may not be orthogonal to each other.

In some examples, a tolerance may be specified by a cosine value or range of cosine values. The use of cosine values, in some cases, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 113A, 113B, 113C of each of the posture cones 114, 116, 118, respectively, are shown in FIG. 5B as being substantially orthogonal to each other, in other examples, center lines 113A, 113B, and 113C may not be orthogonal to each other, and need not even reside within the same plane. Again, the relative orientation of center lines 113A, 113B, 113C may depend on the actual reference coordinate vector output of the posture state sensor of activity sensors 46 of IMD 14 when patient 12 occupies the respective postures.

In some cases, all of the posture cones may be individually defined based on actual reference coordinate vectors. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another, and need not reside within a same plane.

In addition to upright cone 114, lying back cone 116, and lying front cone 118, posture state space 112 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cones 114, in approximately the same plane as lying back cone 116 and lying front cone 118. Moreover, posture state space 112 may include an inverted cone positioned approximately opposite of upright cone 114. Such a cone indicates that the patient's posture is inverted from the upright posture, i.e., upside down.

In some examples, to detect the posture state of a patient, activity sensors 46 of IMD 14 may determine a sensed coordinate vector based on the posture sensor data generated by one or more posture state sensors, and then analyze the sensed coordinate vector with respect to posture cones 114, 116, 118 of FIG. 5B. For example, in a case in which a posture cone is defined by a reference coordinate vector and a tolerance angle, e.g., tolerance angle "A," activity sensors 46 may determine whether the sensed coordinate vector is within upright posture cone 114 by calculating the angle between the sensed coordinate vector and reference coordinate vector, and then determine whether the angle is less than the tolerance angle "A." If so, activity sensors 46 determines that the sensed coordinate vector is within upright posture cone 114 and detects that patient 12 is in the upright posture. If activity sensors 46 determines that sensed coordinate vector is not within upright posture cone 114, activity sensors 46 detects that patient 12 is not in the upright posture.

Activity sensors 46 may analyze the sensed coordinate vector in posture state space 112 with respect to each individual defined posture cone, such as posture cones 116 and 118, in such a manner to determine the current posture state of patient 12. For example, activity sensors 46 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture cone until a match is detected, i.e., until the sensed coordinate vector is found to reside in one of the posture cones. Hence, a cone-by-cone analysis is one option for posture detection.

In other examples, different posture detection analysis techniques may be applied. For example, instead of testing a sensed coordinate vector against posture cones on a cone-by-cone basis, a phased approach may be applied where the sensed coordinate vector is classified as either upright or not upright. In this case, if the sensed coordinate vector is not in the upright cone, activity sensors 46 may determine whether the sensed coordinate vector is in a lying posture, either by testing the sensed coordinate vector against individual lying posture cones or testing the sensed coordinate vector against a generalized lying posture volume, such as a donut- or toroid-like volume that includes all of the lying postures, and may be defined using an angle or cosine range relative to the upright vector, or relative to a modified or virtual upright vector as will be described. In some cases, if lying postures are defined by cones, the lying volume could be defined as a logical OR of the donut- or toroid-like volume and the volumes of the lying posture cones. If the cones are larger such that some portions extend beyond the lying volume, then those portions can be added to the lying volume using the logical OR-like operation.

If the sensed coordinate vector resides within the donut- or toroid-like lying volume, then the sensed coordinate vector may be tested against each of a plurality of lying posture cones in the lying volume. Alternatively, the posture detection technique may not use lying cones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this case, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, activity sensors 46 may first determine whether patient 12 is generally in a lying posture state or upright posture state by analyzing the sensed coordinate vector in posture state space 112 with respect to an axis 113A for the upright posture state. Axis 113A may correspond to the upright reference coordinate vector. For example, angle "A" may be used to define upright posture cone 114, as described above, and angles "D" and "E" may be used to define the vector space in which patient 12 may be generally considered to be in the lying posture state, regardless of the particular posture state cone, e.g., lying front cone 118, lying back cone 116, lying right cone (not shown), or lying left cone (not shown), in which the sensed coordinate vector falls.

If it is determined that a sensed coordinate vector is not within an angle A of the axis 113A, then it may be determined that the patient is not in the upright posture indicated by the upright posture cone. In this case, it may next be determined whether a sensed coordinated vector is generally in a lying posture space volume, which may be considered somewhat donut- or toroid-like, and may be defined relative to the upright reference coordinate vector 113A. As shown, angles "D" and "E" define the minimum and maximum angle values, respectively, that a sensed vector may form with respect to axis 113A of patient 12 for a determination to be made that the patient is generally in the lying posture state. Again, cosine values may be used instead of angles to determine the positions of sensed coordinate vectors relative to posture cones or other posture volumes, or relative to reference coordinate vectors.

As illustrated, angles "D" and 'E' may be defined with respect to vertical axis 113A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 113A, then it can be determined by activity sensors 46 that the patient is generally in a lying posture. Alternatively, in some examples, an angle C could be defined according to a generally horizontal axis 113C (which may correspond to one of the lying reference coordinate vectors). In this case, if a sensed vector is within angle C of axis 113C, it can be determined by activity sensors 46 that the patient is in a lying posture. In each case, the region generally defining the lying posture state may be referred to as a posture donut or posture toroid, rather than a posture cone. The posture donut may generally encompass a range of vectors that are considered to be representative of various lying down postures.

As an alternative, activity sensors 46 may rely on cosine values or a range of cosine values to define the posture donut or toroid with respect to axis 113A. When the sensed vector falls within the vector space defined by axis 113A and angles "D" and "E", or produces a cosine value with the reference coordinate vector 113A in a prescribed range, activity sensors 46 may determine that patient 12 is generally in a lying posture state. For example, if the sensed vector and reference coordinate vector 113A produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture cone 114 defined by angle A, and the second range may be correspond to cosine values that would be produced by vectors in the posture donut defined by angles D and E.

When the sensed vector fall within the vector space defined by axis 113A and angles "D" and "E", as indicated by angle or cosine value, activity sensors 46 may then determine the particular lying posture state occupied by patient 12, e.g., lying front, lying back, lying right, or lying left. To determine the particular lying posture state occupied by patient 12, activity sensors 46 may analyze the sensed vector with respect to reference coordinate vectors for individual lying posture state cones, e.g., lying front cone 116, lying back cone 118, lying right cone (not shown), and lying left cone (not shown), using one more techniques previously described, such as angle or cosine techniques. For example, activity sensors 46 may determine whether the sensed coordinated vector resides within one of the lying posture state cones and, if so, select the posture state corresponding to that cone as the detected posture state. In various examples, any determination of a cone, such as cone 114, 116, 118 as representative of a current posture for a patient may then be compared to a set of postures that are predefined as "sleep postures" for the patient to determine if the patient's current posture is a "sleep posture" for that specific patient. If the current determined posture for a patient during a recharging process of power sources implanted within the patient is determined to be a "inactive posture," this determination, in some examples in conjunction with additional sensed or predetermined parameters associated with the patient, may be used by one or more processors, such as processing circuitry 30 of IMD 14 and/or processing circuitry 50 of external charging device 20 to further control the power level being applied to the recharging process.

FIG. 5C illustrates an example posture state space 115 that is a three-dimensional space substantially similar to posture state space 112 of FIG. 5B. Posture state space 115 includes upright posture cone 117 defined by reference coordinate vector 127. The tolerance that defines upright posture cone 117 with respect to reference coordinate vector 127 may include a tolerance angle or cosine value, as described above. In contrast to determining whether a sensed coordinate vector resides in a lying cone, FIG. 5C illustrates a method for detecting a lying posture based on proximity of a sensed coordinate vector to one of the reference coordinate vectors for the lying postures.

As shown in FIG. 5C, posture state space 115 includes four reference coordinate vectors 119, 121, 123, 125, which are associated with lying left, lying right, lying front, and lying back posture states, respectively. Activity sensors 46 may have defined each of the four reference coordinated vectors 119, 121, 123, 125 based on the output of one or more posture sensors while patient 12 occupied each of the corresponding posture states. Unlike lying front and lying back posture cones 118, 116 in the example of FIG. 5B, the posture state reference data for the four defined posture states corresponding to reference vectors 119, 121, 123, 125 of FIG. 5C need not include angles defined relative to the respective reference vector in a manner that defines a posture cone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, activity sensors 46 may determine whether a sensed coordinate vector is within upright posture cone 117 by analyzing the sensed coordinate vector in view of the tolerance angle or cosine value(s) defined with respect to upright posture reference coordinate vector 127, or whether the sensed vector is within a posture donut or toroid defined by a range of angles (as in FIG. 5B) or cosine values with respect to upright posture reference coordinate vector 127, in which case posture state module 846 may determine that patient 12 is in a general lying posture state.

If activity sensors 46 determines that patient 12 is occupying a general lying posture state, activity sensors 46 may then calculate the cosine value of the sensed coordinate vector with respect to each lying reference coordinate vectors 119, 121, 123, 125. In such a case, activity sensors 46 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 123 as the adjacent vector is the largest value of the four cosine values, the sensed vector may be considered closest in proximity to lying front reference vector out of the four total reference vectors 119, 121, 123, 125. Accordingly, activity sensors 46 may determine that patient 12 is occupying a lying front posture state.

In some examples, activity sensors 46 may determine whether patient 12 is generally in a lying posture state based on the relationship of a sensed vector to upright reference vector 127. For example, as described above, a lying posture donut or toroid may be defined with respect to upright posture reference vector 127, e.g., using angles D and E as in FIG. 5B. Such a technique may be appropriate when lying posture reference vectors 119, 121, 123, 125 define a common plane substantially orthogonal to upright posture reference vector 127. However, the lying posture reference vectors 119, 121, 123, 125 may not in fact be orthogonal to the upright reference coordinate vector 127. Also, the lying posture reference vectors 119, 121, 123, 125 may not reside in the same plane.

To account for non-orthogonal reference vectors, in other examples, a lying posture donut or toroid may be defined with respect to a modified or virtual upright reference vector 129 rather than that actual upright posture reference vector 127. Again, such a technique may be used in situations in which the lying reference vectors 119, 121, 123, 125 are not in a common plane, or the common plane of reference vector 119, 121, 123, 125 is not substantially orthogonal to upright reference vector 127. However, use of the example technique is not limited to such situations.

To define virtual upright reference vector 129, activity sensors 46 may compute the cross-products of various combinations of lying reference vectors 119, 121, 123, 125 and average the cross-product values. In the example of FIG. 5C, activity sensors 46 may compute four cross products and average the four cross product vectors to yield the virtual upright vector. The cross-product operations that may be performed are: lying left vector 119×lying back vector 125, lying back vector 125×lying right vector 121, lying right vector 121×lying front vector 123, and lying front vector 123×lying left vector 119. Each cross product yields a vector that is orthogonal to the two lying reference vectors that were crossed. Averaging each of the cross-product vectors yields a virtual upright reference vector that is orthogonal to lying plane 131 approximately formed by lying reference vectors 119, 121, 123, 125.

Using virtual upright reference vector 129, activity sensors 46 may define a lying posture donut or toroid in a manner similar to that described with respect to upright reference vector 127, but instead with respect to virtual upright reference vector 129. In particular, when activity sensors 46 determines that the patient is not in the upright posture, the posture state module determines whether the patient is in a lying posture based on an angle or cosine value with respect to the virtual upright reference vector 129.

Activity sensors 46 may still determine whether patient 12 is in an upright posture state using upright posture cone 117. If activity sensors 46 determines that patient 12 is occupying a general lying posture state based on the analysis of the sensed coordinate vector with respect to virtual upright reference vector 129, activity sensors 46 may then calculate the cosine value of the sensed coordinate vector (as hypotenuse) with respect to each lying reference coordinate vectors 119, 121, 123, 125 (as adjacent).

In such a case, activity sensors 46 determines the particular lying posture state of patient 12, i.e., lying left, lying right, lying front, lying back, based on which cosine value is the greatest of the four cosine values. For example, if the cosine value calculated with the lying front reference vector 123 is the largest value of the four cosine values, the sensed vector may be considered closest in proximity to lying front reference vector out of the four total reference vectors 119, 121, 123, 125. Accordingly, activity sensors 46 may determine that patient 12 is occupying a lying front posture state.

Additionally, posture state definitions are not limited to posture cones. For example, a definition of a posture state may involve a posture vector and a tolerance, such as a maximum distance from the posture vector. As long as a detected posture vector is within this maximum distance from the posture vector that is included in the definition of the posture state, patient 12 may be classified as being in that posture state. This alternative method may allow posture states to be detected without calculating angles, as is exemplified above in the discussion related to posture cones.

Further to the foregoing, posture states may be defined that are specific to a particular patient's activities and/or profession. For instance, certain postures that are associated with postures the patient normally assumes when sleeping may be designated and pre-defined as "inactive postures" for that particular patient. The cone angle or other tolerance value selected for this posture state may be specific to the particular posture state definition for this patient. In this manner, the defined posture states may be tailored to a specific user, and need not be "hard-coded" in the IMD.

In some examples, individual posture states may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 5B and 5C to define a donut, toroid or other volume. One program group or common set of therapy parameter values may apply to all posture states in the same merged cone, according to the linking status of the posture states, as directed via external programmer 24.

Merging posture cones or otherwise linking a plurality of posture states together may be useful for example in which a common set of therapy parameter values provides efficacious therapy to patient 12 for the plurality of posture states, or for example a set of postures all defined as "inactive postures" for patient 12. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a "donut" or toroid that would be used instead of separate comes 116 and 118, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

The foregoing describes use of one or more activity sensors 46 of IMD 14 which may be used to determine activity and/or posture of patient 10. In some examples, external charging device 20 may carry one or more activity sensors. In such examples, posture reference vectors may be captured by circuitry within external charging device while patients occupy respective posture states and external charging device 20 is affixed to the patient is a substantially predetermined orientation. Assuming external charging device is donned in a substantially same orientation during each recharge session, processing circuitry within external charging device 20 may utilize the carried activity sensors to determine patient activity and/or posture by applying the same or similar techniques as those discussed above in regards to activity sensors 46 carried by IMD 14 to determine patient activity.

In some cases, both activity sensors 46 and activity sensors carried by external charging device 20 may be used to determine patient posture. For instance, activity sensors 46 may be used as the primary means of determining patient posture and/or activity, with sensors of external charging device 20 being used as confirmation of that posture and/or activity. In another example in which IMD 14 does not carry activity sensors 46, the activity sensors of external charging device 20 may determine patient activity and/or posture. While some examples below assume that activity sensors 46 reside within IMD 14, it should be understood this is illustrative only, and it will be understood that such sensors may alternatively or additionally be carried by external charging device 20 (e.g., within housing 21 or by energy transfer device 23.)

Regardless of the technique or techniques used to determine current posture associated with a patient, tracking the changes in the posture(s) assumed by the patient over a period of time may also be used to or as part of determining an activity level for the patient. For example, a sliding window of time having a pre-defined timespan may be set to include the current time and a pre-defined timespan subsequent to the current time. The occurrence of any transition(s) between posture states made by the patient may be tracked during this sliding window of time, and the occurrence of at least one transition, or a minimum number of transitions, from one posture state to another posture state may be tracked. The occurrence of at least one or a minimum number of transitions made by the patient during the sliding window of time may be used to determine and activity level associated with the patient for the current time. By way of example, a sliding window of time is set to have a pre-defined time span of three minutes. At any given current time during a recharging process, the sliding window of time would include the period of time three minutes prior to the current time. The occurrence of any transitions from one predefined posture to a different pre-defined posture state for the patient may be tracked on a rolling basis for the time span of the sliding window. For any particular current time, if at least a minimum number of transitions, including one transition or some threshold number of posture transitions has occurred during the timespan defined by the sliding window, then the patient status is considered to be "active." If on the other hand, for any given current time the minimum number of posture transitions, for example no posture transitions have occurred during the timespan defined by the sliding window, that the patient status is considered to be "inactive."

A change in a patient status from "active" to "inactive" during a recharging process may prompt further control of the power level being applied to the recharging process, such as a lowering of the power level or removal altogether of the power being applied to the recharging process. In some examples, a change in the patient status from "active" to "inactive" will only result in lowering or removal of the power being applied to the recharging process if the patient does not response to a prompt, as described herein, asking the patient to confirm that the patient is awake. In various examples, the tracked changes in the posture of a patient may be one factor that may be used in conjunction with other factors, such as other sensed and/or predetermined parameters, used to make the determination of the activity level and a patient status associated with a patient participating in a recharging process.

Figure 6:
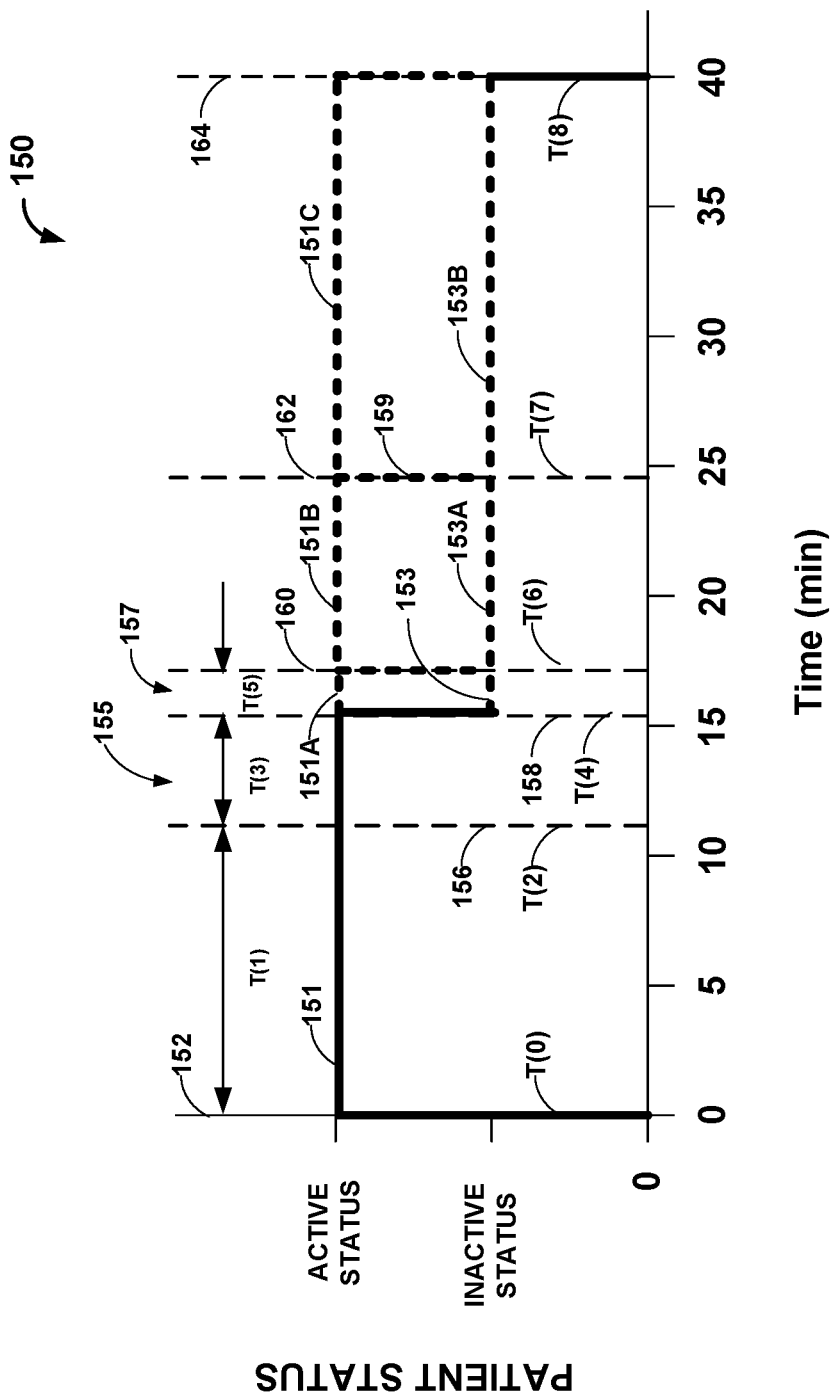
FIG. 6 is a graph of example patient statuses determined during a recharging process in accordance with various techniques described in this disclosure.

FIG. 6 illustrates a graph 150 of example activity statuses that may be monitored for and determined relative to a patient during a recharging process of an IMD implanted in the patient. In FIG. 6, the horizontal axis of graph 150 represents time in minutes of an illustrative recharging process that begins at time T(0), and extend for a time span of forty minutes, ending at time T(8) as indicated at vertical dashed line 164. The forty-minute time span for a recharging process is illustrative and non-limiting, wherein in various examples the recharging process may extend over a time period of more or less than the time span of forty minutes as illustrated in FIG. 6. A vertical axis of graph 150 represents different statuses that may be monitored for and detected with respect to a patient during a recharging process of an IMD implanted in the patient.

At time T(0) in graph 150, as represented by vertical line 152, the recharging process is initiated, and the status associated with the patient is determined to be an "active" status. A determination that the patient status is an "active" status may be made based on any of the activity level determination techniques described herein and any equivalents thereof, including based on one or more parameters associated with the patient as provided by devices, such as activity sensors 46 included in the IMD being recharged, and/or based on other signals provided by sensors, such as sensors 26 shown in FIG. 1, and/or any of the sensor circuitry of IMD 14 as shown and described with respect to FIG. 2. Additional parameters, such as one or more predefined parameters, may also be used in conjunction with the signals in order to determine the patient status.

Referring again to graph 150 of FIG. 6, in various examples the activity level of the patient during the recharging process may be used to determine a status associated with the patient, such as an "active" status or an "inactive" status. The determination of the patient status, for example as "active" or "inactive," may be indicated by the value of an activity signal produced by the IMD, or, in some cases, in combination with activity signals produced by the external charger or an external device such as a programmer. The activity level may be based on these activity signals and any of the activity level determination techniques described herein, and any equivalents thereof. The activity signal associated with the patient undergoing the recharging process as illustrated in graph 150 may indicate that, after initiating the recharging process, the patient status remains at an activity level defined as "active," as illustrated by the horizontal line 151 and time period T(1) shown in graph 150.

At some time during the recharging process, illustratively shown as time T(2) and indicated by vertical dashed line 156, a determination is made that the patient undergoing the recharging process has transitioned from an activity level that is classified as an "active" status to an activity level where no activity, at least based on some minimum threshold level of activity, is still being detected. In various examples, this determination is made by comparing the current value(s) for one or more parameters, including sensed and/or predetermined parameters associated with the patient, to one or more threshold values and/or to predefined range(s) of values for these one or more parameters. A determination that the patient has transitioned from an activity level designated as an "active" status to an activity level that no longer corresponds to the "active" status for the patient in some examples initiates a time period T(3), corresponding to time period 155 in graph 150, which begins at time T(2) and ends at time T(4). During time period T(3), the activity level of the patient is monitored, and a status of the patient during time period T(3) is determined. The activity level of the patient during time period T(3) may be based on a same set of parameters used to determine that the status of the patient has changed at time T(2), or may be a different set of parameters used to determine a transition of the level of activity of the patient at time T(2). For example, the transition of the activity level of the patient at time T(2) may be based on a change in the current posture of the patient to a posture predefined as an "inactive" posture. Once the determination of a transition of the activity level of the patient has been made at time T(2), a different set of parameters, for example parameters including a heartrate, a respiration rate, and/or movements associated with the patient during time period T(3) may be monitored to determine an activity level of the patient throughout time period T(3).

In some examples, at the end of time period T(3) if the activity level of the patient throughout time period T(3) is determined to correspond to an "inactive" status, the activity status associated with the patient is changes to indicate an "inactive" status for the patient, as illustrated in graph 150 by line 151 dropping to the level indicated as an "inactive" status, shown as horizontal line 153 beginning at time T(4). In the alternative, if during time period T(3) the monitored activity level associated with the patient does not correspond to the "inactive" status based on the parameters being monitored during time period T(3), then the activity signal associated with the patient at the end of time period T(3) may not be changed to indicate an "inactive" status, and may remain at a level indicative of the "active" status for some addition duration of the recharging process, as illustrated by dashed line(s) 151A and/or 151B and/or 151C in graph 150. During time period T(3), if the activity level of the patient transitions back and forth between an activity level that corresponds to the "active" status and the "inactive" status, each transition back to the activity level that corresponds to the "inactive" status may be used to retrigger a new time period equivalent to the time period T(3), during which the activity level of the patient is monitored based on the one or more parameters used to determine the activity status of the patient throughout time period T(3). As such, time period T(3) may become a sliding window having a predefined duration in time, and wherein the start of time period T(3) may be retriggered each time the activity level of the patient transitions from a status corresponding to an "active" status to an activity level that does not correspond to the "active" status. The predefined duration for time period T(3) is not limited to any particular time period, and may be determined based on values for time periods stored in memory in the IMD and/or in the external charging devices. In some examples the predefined time period for time period T(3) may range from 5 to 10 minute(s).

At some time during the recharging process, illustratively shown as time T(4) and indicated by vertical dashed line 158, a determination is made that the patient undergoing the recharging process has transitioned from an activity level that is classified as an "active" status to an activity level where no activity, at least based on some minimum threshold level of activity, is still being detected. In various examples, this determination is made by comparing the current value(s) for one or more parameters, including sensed and/or predetermined parameters associated with the patient, to one or more threshold values or predefined ranges of values for these one or more parameters, respectively. A determination that the patient has transitioned from an activity level designated as an "active" status to the "inactive" status for the patient is illustrated in graph 150 by line 151 dropping to the level indicated as an "inactive" status, shown as horizontal line 153 beginning at time T(4). This change in the activity signal to indicate a patient status of "inactive" may remain for some addition portion(s) of the recharging process, as illustrated by dashed lines 153, 153A, and/or 153B in graph 150.

The determination to change the patient status to the "inactive" level may or may not include the time period T(3) described above. In some examples, the determination to change the patient status to the "inactive" status may occur based on monitoring the activity level over time period T(3) prior to time T(4). In other examples, the determination to change the patient status to the "inactive" status may occur without the preceding time period T(3), and may be based on change(s) in the value(s) associated with one or more of the monitored parameters used to determine the activity level of the patient at time T(4) specifically.

At the time T(4), the status of the patient is determined to be an "inactive," a device such as the IMD being recharged by the recharging process may be configured to generate an activity signal that indicates that the patient status is now determined to correspond to an "inactive" status. This "inactive" status output signal may be transmitted at time T(4) from the IMD to one or more external devices, such as an external charging device providing the power being used to recharge the rechargeable power source of the IMD. In some examples the change in status to "inactive" may result in a value associated with the patient status and stored in the IMD to be set to value corresponding to the "inactive" status. As described above, an external device such as recharging device 20 may poll the value of the patient status stored in the IMD. Based on receiving the "inactive" status output signal during the recharging process, or based on polling the patient status and determining that the polled value for the patient status is representative of the "inactive" status, the external charging device may modify the power level being used for the recharging process in order to reduce the possibility of an unsafe level of heating generated at the primary coil, and/or in the tissue of the patient. In some examples, the external charging device may terminate the charging process at some time before the full forty-minute time span has occurred based on receipt of the "inactive" status output signal prior to time T(8). A determination to continue the recharging process at a lower power level verse termination of the recharging process in response to a determination of an "inactive" status for the patient undergoing the recharging process may be based on one or more additional parameters, including but not limited to a state-of-charge of the power source being recharged and/or the current therapy stimulation requirements in some examples, as further described below with respect to FIGS. 7A-7B.

Referring again to FIG. 6, once the status of the patient has transitioned to an "inactive" status, one or more parameters, such as sensed parameters and/or predetermined parameters associated with the patient, as described above, may continue to be monitored to determine an activity level for the patient. At some point following time T(4), a determination may be made that the status of the patient has transitioned from an "inactive" status back to an activity level determined to correspond to an "active" status. For example, at time T(7), as represented by vertical dashed line 162, a determination is made that that status of the patient has transitioned from the "inactive" status to a status corresponding to an "active" status, as represented by dashed line 159 rising from line 153 to the "active" status level represented by horizontal dashed line 151C in graph 150. The determination that the patient status has returned to the "active" status may be based on continuing to monitor one or more parameters, including sensed parameters and/or predefined parameters associated with the patient. For example, a determination that the patient has transitioned from a posture predefined as an "inactive" posture to a posture that is not one predefined as an "inactive" posture may be considered a parameter that results in the patient status transitioning from the "inactive" status to an "active" status. In another example, an input provided by the patient, such as an input provided by the patient to the recharging device and/or an input provided by the patient to an external device such as a programmer, may be used as a basis that allows the activity level of the patient, and thus the activity signal, to transition from the "inactive" status to the "active" status.

In various examples, the transition back to the "active" status may cause the IMD to generate and transmit to the recharging device and/or an external device such as a programmer an activity signal indicated of the "active" status for the patient undergoing the recharging process. In some examples the change in status to "active" status may result in a value associated with the patient status and stored in the IMD to be set to value corresponding to the "active" status. As described above, an external device such as recharging device 20 may poll the value of the patient status stored in the IMD. Based on this updated activity signal, or based on polling the patient status and determining that the polled value for the patient status is representative of the "active" status, the external device may be configured to adjust the power settings, for example to raise the power level being applied to the recharging process.

In some examples, at time T(4) and based on a determination that the status of the patient has transitioned from the "active" status to an activity level corresponding to the "inactive" status, that activity signal associated with the status of the patient may not be immediately changed to represent the "inactive" status, Instead, at time T(4), the activity signal remains at the "active" status level, and a timer may begin to time a time period starting at time T(4) and ending at time T(6) and vertical dashed line 160, indicated as time period T(5) and reference number 157 in graph 150. In this alternative example, at time T(4), a device such as IMD 14 may generate the "inactive" status output signal, and transmit the signal to one or more external devices, such as external charging device 20, and/or another external device, such as external programmer 24. In response to receiving the "inactive" status output signal, the external device(s) may be configured to provide a prompt, such as a visual prompt on a display screen, and/or a tactile and/or an audio prompt that requests that the patient confirm that the patient is awake. The prompt may be provided in combination with an audible signal, such as a "ping" or "beeping" sound, or other audio signal that may be heard by the patient if the patient is awake, or may also be designed to wake the patient in the event the patient is asleep. The prompt in some examples may also include additional queues, such as a vibrational queue, designed to vibrate a device such as the patient's smartphone or other programmer device, so alert the patient to the output of the "inactive" output status signal.

Once the "inactive" status output signal has been transmitted from the IMD, the time period T(5) is initiated. In some examples, if the time period T(5) expires, as represented by time T(6) and vertical dashed line 160, and the IMD or the external charging device has not received a reply that was input by the patient in response to the prompt, the patient status is then changed to be "inactive" at time T(6), as illustrated by horizontal line 151A dropping to the level indicated by horizontal dashed line 153A at time T(6). In these instances, the IMD and/or the external charging device may be configured to provide additional signals to cause the power level of the recharging process to be lowered and/or removed altogether following time T(6), in some instances for the remainder of the recharging process ending at time T(8), as represented by horizontal dashed lines 153A and/or 153B. In the alternative, if during time period T(5) a response to the prompt, for example an input provided by the patient, is received in response to the prompt, the activity level of the patient may no longer be considered to be "inactive," and the status of the patient may not be changed from "active" to "inactive" at the end of time period T(5), as represented by horizontal dashed line 151B. In some examples, the determination that the activity level of the patient at the end of time period T(5) may also be based on whether a change in some monitored parameters, such as a transition in the current posture of the patient from an "inactive" posture to some posture that is not predefined to the an "inactive" posture, occurs during time period T(5). For example, if during time period T(5) a transition in the status of one or more parameters, such as the current posture of the patient, is determined to indicate that the status of the patient should no longer be classified as "inactive," then the status of the patient may not be changed from "active" to "inactive" at the end of time period T(5), and may remain at the "active" status level, as represented by dashed line 151B. The indication of the "active" status following time T(6) may remain for some addition duration of the recharging process, as illustrated by horizontal dashed line(s) 151B and/or 151C in graph 150.

In various examples, an external device, such as external charging device 20 illustrated and described in FIG. 1, polls the value of the patent status determined by IMD 14, and based on the determined status, performs the process including generating and providing the prompt to the patient, timing time period T(5), monitoring for a response during time period T(5), and determining whether to lower or otherwise modify the power level(s) being provided to the recharging process based on whether or not a response is detected during time period T(5). In some examples, the duration of time period T(5) is a predefined duration of time. The duration of time period T(5) is not limited to any particular time period, and may be determined based on values for time periods stored in memory in the IMD and/or in the external charging devices. In some examples the predefined time period for time period T(5) may range from 2 to 5 minute(s).

Figure 7A:
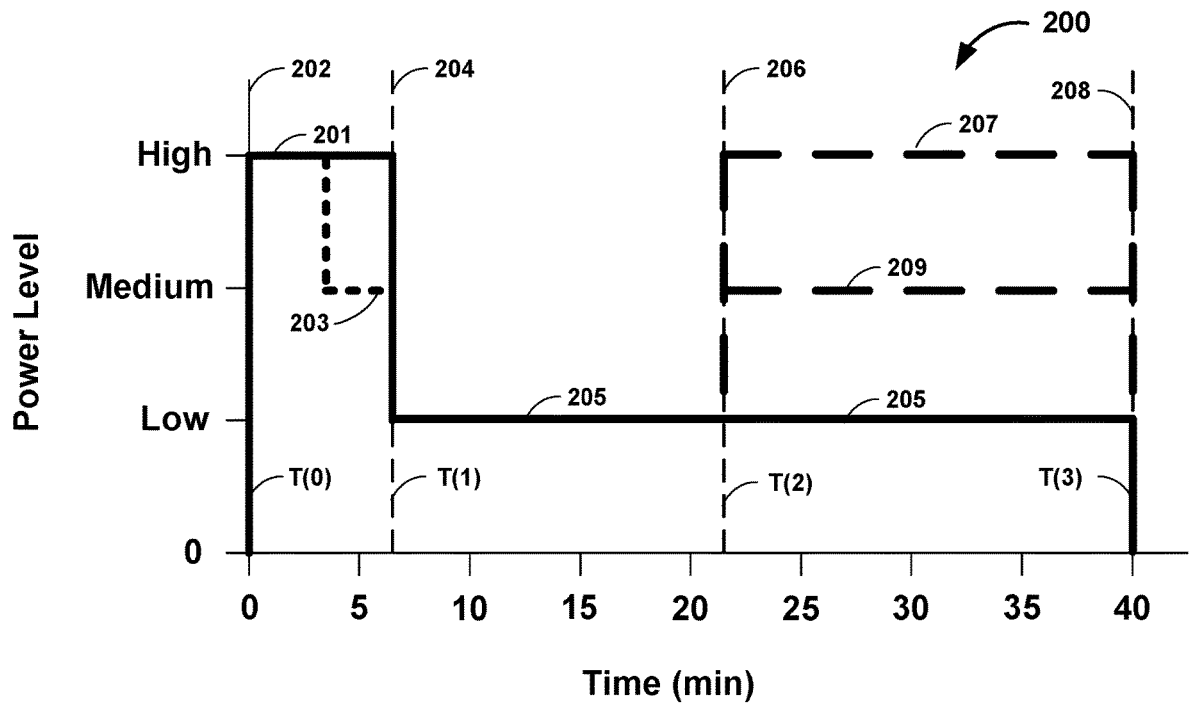
FIGS. 7A and 7B are graphs of example selected power levels utilized during a recharging process in accordance with various techniques described in this disclosure.
Figure 7B:
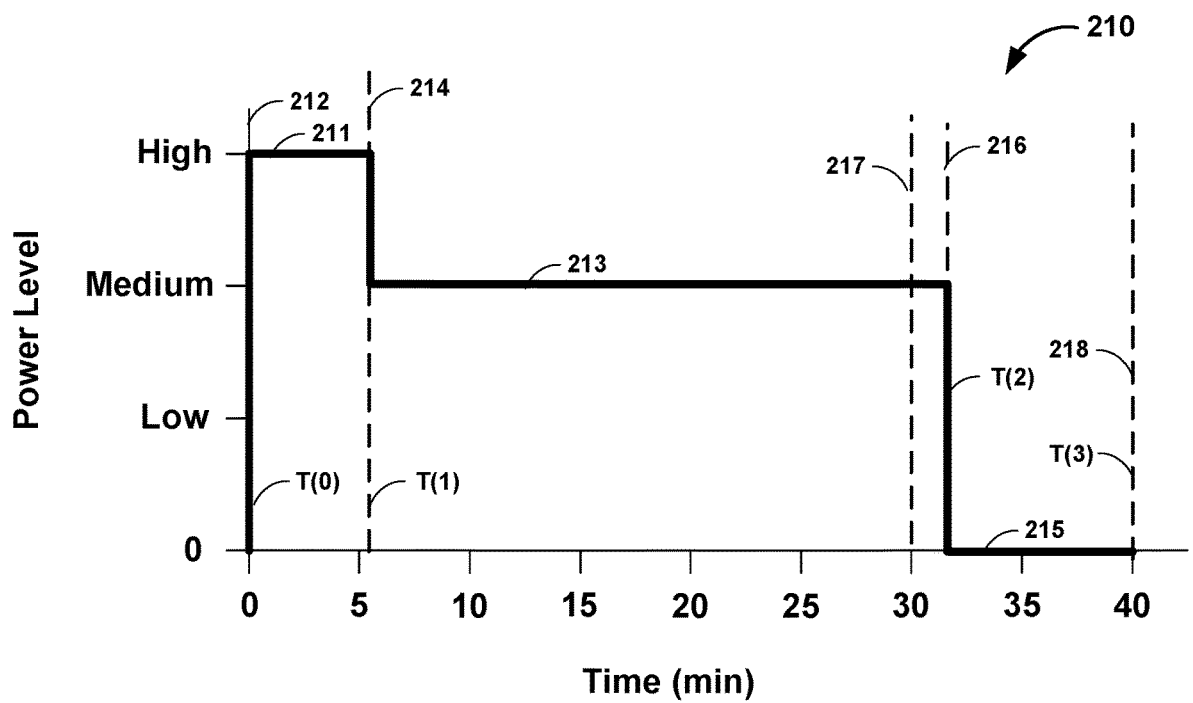

FIGS. 7A and 7B are graphs 200, 210 of example selected power levels used for recharging power source(s) of an IMD and/or implanted sensors in accordance with the techniques described in this disclosure. Each of graphs 200, 210 includes a vertical axis representative of various recharging power levels including a "high" power level, a "medium," power level, and a "low" power level. The "zero" power level along the vertical axis at the origin of graphs 200, 210 represent no recharging power being provided to the recharging process. The power levels represented as the "high," "medium," and "low" power levels are not limited to being any particular power levels, and are each representative of a level of power being provided that is relative to the other power levels. For example, a "high" power level represents a charging power level providing a larger amount of power to the recharging process, for example by an external charging device, than would be provided by the "medium" power level. The "medium" power level represents a charging power level that provides a larger amount of power to the recharging process, for example by the external charging device, as compared to the power level provided by the "low" power level.

In general, the "high" power level would also generate a larger amount of heating, for example in the IMD being recharged, or generate a higher amount of heating to the tissue and/or at the primary coil being used to provide the recharging power, as compared to the "medium" power level. Similarly, in general the "medium" power level would generate a larger amount of heating, for example in the IMD being recharged, or generate a larger amount of heating to the tissue and/or at the primary coil being used to provide the recharging power, as compared to the "low" power level. The "zero" power level represents no power being applied to the recharging process, and thus would not contribute to additional heat being generated by the recharging process when the "zero" power level is applied.

In addition, each of graphs 200, 210 includes a horizontal axis representative of time, in minutes, during which the illustrative recharging processes may be conducted. The total time span of forty-minutes for the recharging processes illustrated in graph 200 and 210 is intended to be illustrative and not limiting with respect to the time period for a recharging process. In various examples, the time span of a given recharging process depicted by graphs 200 and 210 may occur over a time span that is more or less than forty minutes in duration.

As shown in FIG. 7A, a recharging process is initiated at time T(0), shown as vertical line 202, and illustrates the power level along the vertical axis rising from "zero" to a "high" power level at that time. In some examples, this "high" power level of recharging, represented by horizontal line 201, continues during the time period between time T(0) ending at time T(1), time T(1) represented by the vertical dashed line 204. During this time period between time T(0) and T(1), the status of the patient undertaking the recharging process of implanted devices is monitored, and is determined to be "active" through this time period. As such, the power level being applied during the recharge process may remain at the "high" level. In the alternative, at some point during the time period between time T(0) and T(1), some other factors, based for example on thermal dose and/or sensed temperatures related to the charging process, may cause the recharging process to shift from the "high" power level to the "medium" power level, as indicated by dashed lines 203. Regardless, in the example illustrated in FIG. 7A, a status associated with the patient may remain as an "active" status based on a current posture and/or an activity level determined for the patient during the time period between time T(0) and time T(1).

At time T(1) in graph 200, based on monitoring the status of the patient, a determination has been made that the patient status should be changed from an "active" status to an "inactive" status. The change in status may be determined based on any of the monitored parameters, such as posture and/or activity level, described throughout this disclosure as used for determining a status for the patient relative to a current posture, an activity level, and/or whether the patient may be asleep. Based on the change in patient status to "inactive," the power level applied to the recharging process illustrated in graph 200 is lowered to the "low" power level, as represented by horizontal line 205 at time T(1). In various examples, the determination to continue the recharging process at the "low" power level may be based on a determination of how much of the total time span estimated for the recharging process has been completed.

For example, as shown in FIG. 7A time T(1) corresponding to the change of the patient status to "inactive" occurs at around six minutes into the forty-minute estimated total time to perform the recharging process. In some instances, if the change in status of the patient to an "inactive" status occurs before a predetermined threshold time with respect to the recharging process, then the recharging process is configured to automatically continue at a "low" power level or a lower power level, as indicated by horizontal line 205 in graph 200. The predetermined threshold time limit for determining whether to continue the recharging process when a patient status changes to "inactive" is not limited to any particular time, and for example may be set to a time limit of having at least thirty minutes (e.g., approximately three-fourths) of the total estimated recharging time of forty minutes completed. If the "inactive" status of the patient occurs at a time less than the threshold time, the recharging process continues at the "low" or a lower power level, and if the "inactive" status to the patient occurs at a time after the threshold time limit, a different modification to the recharging process may occur, for example stopping the recharging process.

In some examples, after the power level of the recharging process is set to the "low" power level, the same or a different set of parameters related to the patient may continue to be monitored, and if the patient status is determined again be "active" rather than "inactive," the power level used for some or all of the remainder of the recharging process may be raised. For example, at time T(2) as shown in graph 200, a determination may be made that the status of the patient has changed from "inactive" to an "active" status. Based on that determination, the power level used for the charging process may be raised to a higher power level, for example to the "high" power level as represented by horizontal dashed line 207, or to the "medium" power level as represented by the horizontal dashed line 209 in graph 200. The determination as to whether to continue the charging process at the "high" or the "medium" power level may be based on one or more factors, including but not limited to the total current charge level of the power source being recharged and/or the total time remaining to complete the recharging, and/or the current sensed or estimated temperatures of the IMD, the tissue, and/or the primary coil associated with the recharging process.

In various examples, if the status of the patient following time T(1) in graph 200 remains as "inactive," the power level of the recharging process may remain at the "low" power level for the remainder of the charging process, generally indicated as ending at the vertical dashed line 208 at time T(3). The power level used for the recharging process at the "low" power level is set to a power level determined to be safe with respect to temperature and patient safety even in instances where the patient may have fallen asleep with the primary coil located between the skin of the patient and some other insulative layer of material, such as a mattress of a bed or a cushion of a couch. Further, during the time period(s) of the recharging process where the power level is controlled based on the patient status being an "active" status, decisions regarding using the "high" the "medium" or even the "low" power levels may be based on other factors, such as but not limited to the thermal dose and/or sensed/estimated temperatures associated with the recharging process, and may be modified during the recharging process based on one or more determinations based on these factor other than the activity status determined of the patient.

In various examples, the end of the recharging period, represented as time T(3) in graph 200, may vary based on the variations in the power levels applied throughout the charging process. For example, as shown in FIG. 7A, the change to the "low" power level for the recharging process occurs relatively early in the total time span between time T(0) and T(3). The lower power level applied to the recharging process between time T(1) and T(3), as represented by horizontal line 205, may mean that the charge level of the power source being recharged may not be at the expected level when time T(3) occurs. Thus, based on the charging level of the power source as determined at time T(3), the recharging time may be extended beyond the forty minutes indicated in graph 200. In such instances where higher power levels are maintained throughout more of the recharging process than as illustrated in graph 200, the charging level of the power source may indicate that the power source is fully recharged at some time prior to the forty-minute time period estimated for the recharging process illustrated in graph 200. In examples where the power source is determined to be fully charged prior to the forty-minute time period, the recharging process may be halted at some time prior to the estimated forty-minute time period shown in FIG. 7A.

FIG. 7B illustrates another possible set of power level changes associated with a recharging process, as illustrated by graph 210. As shown in FIG. 7B, a recharging process is initiated at time T(0), shown as vertical line 212, and illustrates the power level along the vertical axis rising from "zero" to a "high" power level at that time. In some examples, this "high" power level of recharging, represented by horizontal line 211, continues during the time period between time T(0) ending at time T(1), time T(1) represented by vertical dashed line 214. During this time period between time T(0) and T(1), the status of the patient undergoing the recharging process is monitored, and is determined to be "active" during this time period. In addition, other factors, such as thermal dose and/or temperatures associated with the recharging process, may also be monitored. Based on these monitored parameters, the power level being applied during the recharge process may remain at the "high" level between time T(0) and T(1) as illustrated by graph 210.

At time T(1) as shown in graph 210, the power level being applied to the recharging process is lowered from the "high" power level to the "medium" power level. In some examples, this reduction in the applied power level is performed even if the activity level associated with the patient remains as "active." This drop in the applied power level at time T(1) may for example result from other factors, such as thermal dose calculations, or for example a rise in the temperature(s) associated with the recharging process. As shown in graph 210, the "medium" power level continues to be applied in the recharging process beginning at time T(1) through the point in time T(2), time T(2) represented by vertical dashed line 216.

In various examples, at time T(2) a determination is made that the patient status has changed from an "active" status to an "inactive" status. In response to this change in the patient status, the power level applied to the recharging process is reduced to a "zero" level of power being applied to the recharging process, as represented by horizontal line 215, through the remainder of the recharging process, ending at time T(3) as indicted by vertical dashed line 218. In this instance as illustrated in graph 210, a determination of the patient status as "inactive" has occurred after a threshold time, for example a threshold time of thirty-minutes (indicated by vertical dashed line 217) following initiation of the recharging process. Therefore, the recharging system may be configured to terminate the recharging process at the time the status changes to "inactive" by lowering the power level to the "zero" level for the remainder of the recharging process. In some examples, the determination to lower the power level being applied to the recharging process to a "zero" power level at the time the status of the patient changes to "inactive," may be based on determining that the power source being recharged has been recharged to a level that exceeds a threshold recharge level, and based on that determination, further recharging while the patient is in the "inactive" status will not occur.

Figure 8:
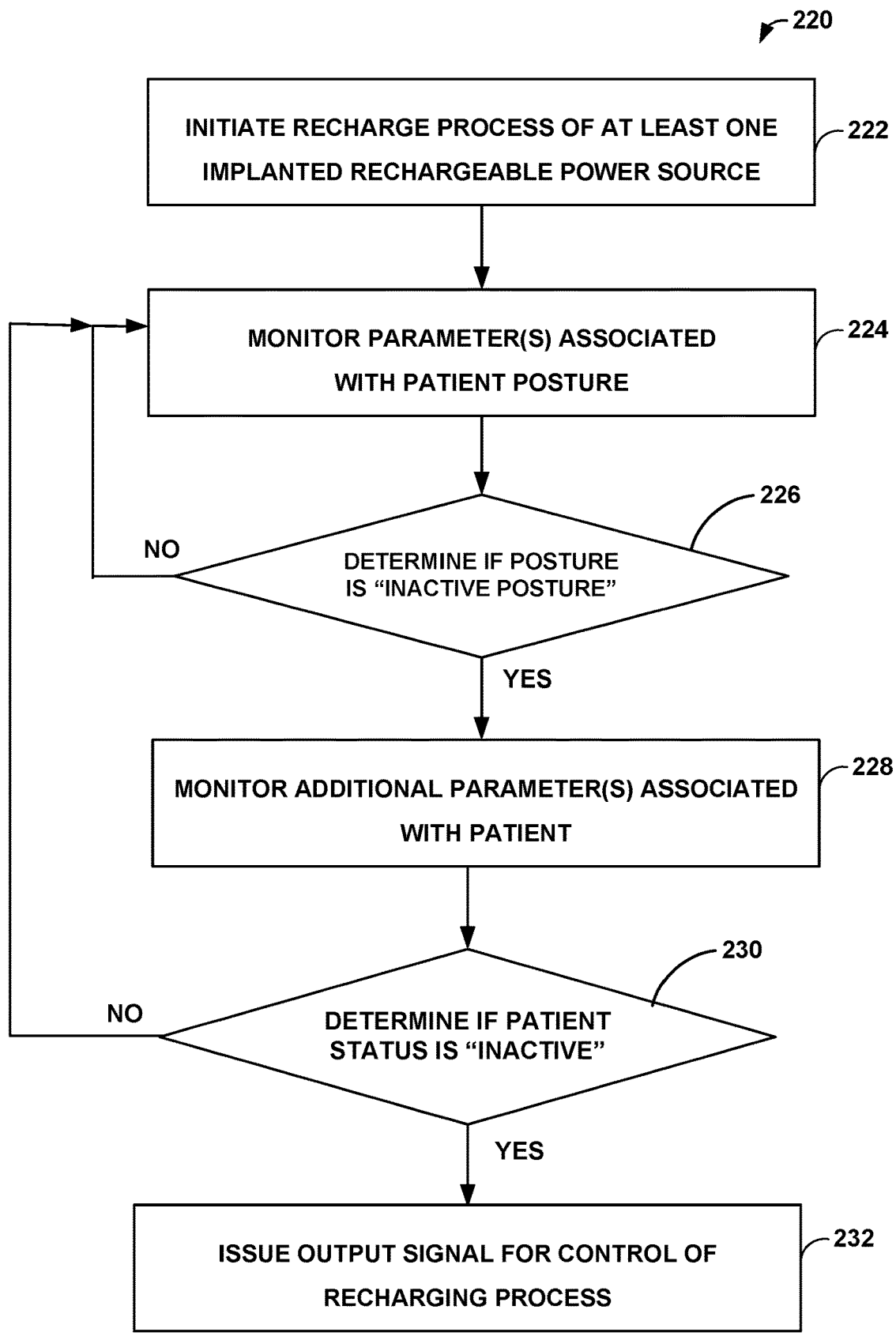
FIG. 8 is a flow diagram that illustrates an example technique for controlling a power level used for recharging a rechargeable power source based a patient status in accordance with various techniques described in this disclosure.

FIG. 8 is a flow diagram 220 that illustrates an example technique for controlling a power level used for recharging a rechargeable power source 18 based on a patient status. Although processing circuitry 30 of IMD will be described as generally performing the technique of FIG. 8, the technique of FIG. 8 may instead be performed by a combination of processing circuitry 30 of IMD 14 and processing circuitry 50 of external charging device 20, or in some cases entirely by processing circuitry 50 of external charging device 20, as may be the case when processing circuitry 50 receives raw data from IMD 14 and/or relies upon a combination of sensor data generated by sensors of external charging device to determine patient activity and posture.

A charging session for rechargeable power source 18 may begin when processing circuitry 50 receives a charge request via external programmer 24, and the recharging process, which may include processing circuitry 50 providing a signal that is transmitted to processing circuitry 30 of IMD 14 implanted within a patient (block 222). Upon initiation of the recharging process, processing circuitry 30 monitors parameters associated with a current posture for the patient (block 224). Monitoring parameters associated with a current posture for the patient may include any of the techniques described in this disclosure, including receiving signal from one or more sensors, such as accelerometers provided by activity sensors 46 and/or sensors 26, and determining a current posture of the patient based on these signals. As discussed above, accelerometers carried by external charging device may be used instead of, or in addition to, the implantable sensors, in which case it will be understood that monitoring and analysis of activity and posture as described with respect to the following steps are performed at least in part by processing circuitry 50.

Processing circuitry 30 is further configured to determine if the current posture determined for the patient is a posture defined as a "inactive posture" for the patient (block 226). In some examples, each of the postures defined as a "inactive posture" for the patient may be stored in memory 32 of IMD 14, or stored and accessed from memory in the external charging device and/or an external programmer. During a recharging process, processing circuitry 30 may access these pre-defined posture states to determine, by comparison, if the current posture state for the patient is any one of the predefined "inactive postures" for the patient. For example, for the patient undertaking recharging of IMD 14, an "inactive posture" state for the patient may be defined as a posture state where the patient is lying down on their back. If the current posture for the patient is determined to not be one of the "inactive postures" defined for the patient, (a "NO" branch of block 226), the method 220 returns to block 224, wherein processing circuitry 30 continues to monitor parameters associated with a current posture for the patient. In the alternative, if processing circuitry 30 determines that the current posture for the patient is one of the postures defined for the patient as a "inactive posture," (the "YES" branch of block 226), method 220 proceeds to block 228.

At block 228, processing circuitry 30 is configured to begin monitoring one or more additional parameters associated with the patient. These one or more addition parameters may include monitoring any of the sensed signals provided by sensors within IMD 14, including signals provided by sensor circuitry 42, temperature sensor 44, activity sensors 46, and/or additional sensed signal provided by sensors external to IMD 14, such as signal provide by one or more of sensors 26. These additional sensed signals may be processed by processing circuitry 30, for example by comparison to threshold values stored in memory 32 of IMD 14, to determine an activity level of the patient. In addition to sensed signals, processing circuitry 30 may also monitor additional predetermined parameters, such as time of day compared to the normal sleep times that are predefined for the patient and stored in memory 32.

Based on the monitored additional parameters, processing circuitry 30 may determine a status for the patient. Based on the determined status for the patient, processing circuitry 30 further determines if the patient status is an "inactive" status (block 230). A determination that the status associated with the patient may be based on any one or a combination of sensed parameters, and/or one or more predetermined parameters associated with the patient as described throughout this disclosure. As determination of a status associated with the patient may include monitoring the parameters over a predefined period of time, and determining that the status of the patient has remained unchanged over that predefined period of time. A determination that the current status associated with the patient at block 230 is not an "inactive" status (the "NO" branch of block 230) caused a return of method 220 to block 224, wherein processing circuitry 30 is configured to continue to monitor a current posture associated with the patient. In the alternative, if the current activity level associated with the patient at block 230 is determined by processing circuitry 30 to be an "inactive" status (the "YES" branch of block 230), method 220 proceeds to block 232.

At block 232, processing circuitry 30 is configured to issue an activity signal as an output signal, for example to one or more external devices such as external charging device 20 and/or external programmer 24. The activity signal issued by processing circuitry 30 may be transmitted to the external devices through a wireless signal provided as an output from telemetry module 36. In various examples, the activity signal may simply provide an "inactive" status output signal to the one or more external devices. In such instances, the external device(s) may be configure to automatically lower the power level being applied to the recharging process, or may in the alternative, be configured to terminate the recharging process, upon receipt of the "inactive" status output signal provided by IMD 14. In various examples, issuing the output signal at block 232 includes processing circuitry 30 providing information including instructions to the external device(s) as to how the external device(s), such as external charging device 20, are to further control the recharging process, or for example may include instructions to terminate the recharging process initiated at block 222 of method 220. In alternative examples, processing circuitry 30 may change and store a value associated with the patient status so that the value indicates the "inactive" status for the patient. The patient status is polled by the external device, and upon polling the patient status and determining that the value associated with the patient status now corresponds to a value of the "inactive" status, the external device may be configured to modify and/or terminate the recharging process.

In various examples, the output signal provided at block 232 includes processing circuitry 30 requesting that a prompt be provided to the patient, requesting that a reply from the patient be provided within a pre-defined time limit following issuance of the prompt signal, the reply being of a type requiring the patient to provide an input indicating that the patient is awake. After issuing this prompt request signal, processing circuitry 30 may also initiate a timer that provides timing of a predefined time period for receiving a response input from the patient. In these examples, processing circuitry 30 may monitor any input received from the external devices, and if the response to the prompt signal is not received by the end of the predefined time period, processing circuitry 30 may then be configured to issue another output signal to the one or more external devices, the additional output signal now including the "inactive status output signal." This issuance of the "inactive status output signal" by processing circuitry 30 may result in lowering of the power level being provided by the recharging process, or termination of the recharging process initiated at block 222 of method 220, as previously described above.

At any time during the execution of one of blocks 224, 226, 228, and 230, processing circuitry 30 may receive a signal indicating that the recharging process initiated at block 222 is being terminated. Processing circuitry 30 is configured to cease further execution of the processing steps illustrated in FIG. 8 upon recipe of this termination signal. In some examples, an external device such as external charging device 20 and/or external programmer 24 may terminate the recharging process that is underway, for example based on an indication that the power source be recharged is fully recharged, or for example based on an indication that a thermal dose limit or a temperature limit associated with the recharging process has been reached, and further recharging should not continue. In some examples, the external device may communicate the decision to terminate the recharging process to IMD 14 and processing circuitry 30, for example via a signal transmitted from the external device that is received at telemetry module 36 of IMD 14. When receiving such a termination signal, processing circuitry 30 may end any processing related to blocks 224, 226, 228, 230, and 232 in order to conserve processing power and time, and to reduce possible power drain of the energy stored in rechargeable power source 18.

Figure 9:
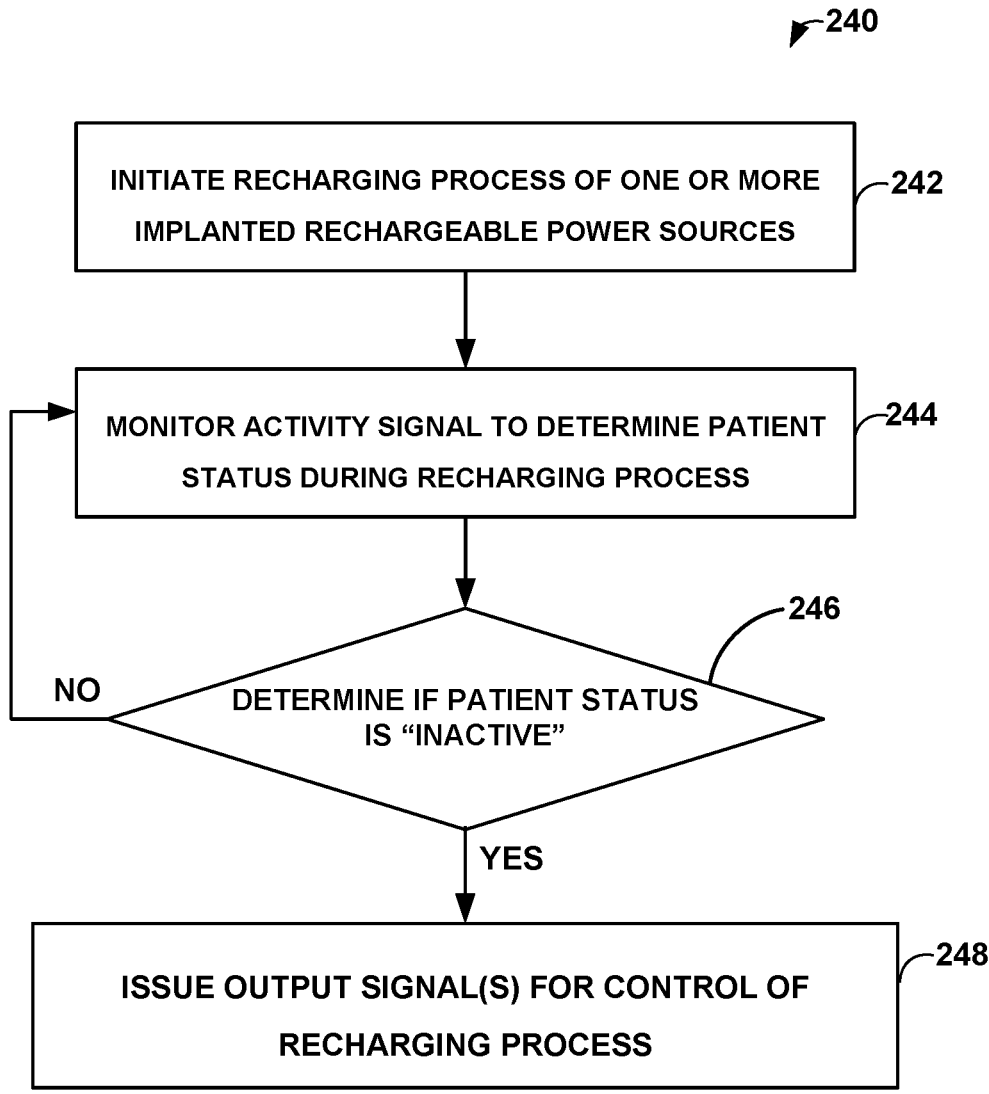
FIG. 9 is a flow diagram that illustrates an example technique for controlling a power level used for recharging a rechargeable power source based a patient status in accordance with various techniques described in this disclosure.

FIG. 9 is a flow diagram 240 that illustrates an example technique for controlling a power level used for recharging a rechargeable power source 18 based on a patient status. Although processing circuitry 30 of IMD will be described as generally performing the technique of FIG. 9, the technique illustrated in FIG. 9 may instead be performed by a combination of processing circuitry 30 of IMD 14 and/or processing circuitry 50 of external charging device 20, in other examples.

A charging session for rechargeable power source 18 may begin when processing circuitry 50 receives a charge request via external programmer 24, which may include processing circuitry 50 providing a signal that is transmitted to processing circuitry 30 of IMD 14 implanted within a patient (block 242). Upon initiation of the recharging process, processing circuitry 30 monitors parameters associated with an activity level for the patient (block 244). Monitoring parameters associated with an activity level for the patient may include any of the techniques described in this disclosure, including receiving signal(s) from one or more sensors, such as accelerometers provided by activity sensors 46 and/or sensors 26, and determining a current posture of the patient based on these signals. Processing circuitry 50 may also monitor parameters associated with an activity level for the patient based on output of external sensors, as described above. The values associated with these monitored parameters may be transmitted to processing circuitry 30 for further analysis in determining a status of the patient.

Processing circuitry 30 is further configured to determine if the activity level for the patient is an activity level that would be defined as an "inactive" status for the patient. For example, a status of "inactive" may be determined to be the current status for the patient if the determined level of activity for the patient over a minimum and predefined time period just prior to the current time includes the patient being at an activity level that would qualify as the "inactive" status throughout the pre-defined time period. Processing circuitry 30 is configured to determine if the current status of the patient has transitioned from an "active" status to an "inactive" status (block 246). In various examples, the determination that the current status for the patient has transitioned to the "inactive" status (the "YES" branch of block 246) is based on the determination of the level of activity of the patient over the pre-defined time period just prior to the current time being at a level of activity consistent with an "inactive" status. If processing circuitry 30 determines that the current status of the patient has transitioned to the "inactive" status at block 246, method 240 proceeds to block 248.

In the alternative, if processing circuitry 30 determines at block 246 that the patient status has not transitioned to the "inactive" status (the "NO" branch of block 246), method 240 proceeds back to block 244, wherein at block 244 processing circuitry 30 continues to monitor one or more parameters used to determine the activity level associated with the patient during the recharging process.

At block 248, processing circuitry 30 may be configured to issues one or more output signals for control of the recharging process in any of the arrangements described above with respect to block 232 in FIG. 8. For example, at block 248 in FIG. 9, processing circuitry 30 may simply issue an "inactive" status output signal to one or more external devices, with or without additional instructions and/or additional information, causing the external devices, such as external charging device 20, to further control the power level being applied to the recharging process, or in the alternative to terminate the recharging process, as described above. In alternative examples, processing circuitry 30 at block 248 is configured to issue the prompt request, and to initiate a timer for timing the period of time allocated for receiving a response to the prompt signal, as described above with respect to processing circuitry 30 and block 232. In a similar manner to that described above with respect to block 232, at block 248 processing circuitry 30 may issue an additional output signal in response to not receiving any reply input by the patient in response to the issuance of the prompt signal, the additional output signal used to control the power level being applied to the recharging process, or to terminate the recharging process initiated at block 242.

At any time during the execution of one of blocks 244, 246, and 248, processing circuitry 30 may receive a signal indicating that the recharging process initiated at block 242 is being terminated. Processing circuitry 30 is configured to cease further execution of the processing steps illustrated in FIG. 9 upon recipe of this termination signal. In some examples, an external device such as external charging device 20 and/or external programmer 24 may terminate the recharging process that is underway, for example based on an indication that the power source be recharged is fully recharged, or for example based on an indication that a thermal dose limit or a temperature limit associated with the recharging process has been reached, and further recharging should not continue. In some examples, the external device may communicate the decision to terminate the recharging process to IMD 14 and processing circuitry 30, for example via a signal transmitted from the external device that is received at telemetry module 36 of IMD 14. When receiving such a termination signal, processing circuitry 30 may end any processing related to blocks 242, 244, 246, and 248 in order to conserve processing power and time, and to reduce possible power drain of the energy stored in rechargeable power source 18.

According to the techniques and devices described herein, a monitored posture and/or an activity level associated with a patient having one or more implanted devices may be used to further control power levels and/or to terminate a recharging process initiated to recharge rechargeable power sources of the implanted devices. The power level used for the recharging process may be reduced based on a determination that the current postures of the patient during the recharging process corresponds to one or more pre-defined posture states for the patient, and/or the activity level of the patient determine of the patient corresponds to either an "active" or an "inactive" status for the patient.

This disclosure is primary directed to control of the wireless transfer of energy between two coils (e.g., inductive coupling). However, one or more aspects of this disclosure may also be applicable to energy transfer involving a physical connection between a charging device and a rechargeable power supply. For example, aspects of this disclosure may be applicable to charging the rechargeable power supply of an IMD by inserting a needle coupled to an external charging device through the skin and into a port of the IMD. Although physical connections for energy transfer may not introduce heat losses due to energy transfer between wireless coils, heat may still be generated and lost to the patient from components within the IMD (e.g., the battery being charged and circuits involved in the recharging of the power supply).

The disclosure also contemplates computer-readable storage media comprising instructions to cause a processor to perform any of the functions and techniques described herein. The computer-readable storage media may take the form of any volatile, non-volatile, magnetic, optical, or electrical media, such as a RAM, ROM, NVRAM, EEPROM, flash memory, or any other digital media. The computer-readable storage media may be non-transitory in that the storage media is not an electromagnetic carrier wave. However, this does not mean that the storage media is not transportable or that it non-volatile. A programmer, such as patient programmer or clinician programmer, may also contain a more portable removable memory type to enable easy data transfer or offline data analysis.

The techniques described in this disclosure, including those attributed to IMD 14, charging device 20, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated, discrete, or analog logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processing circuitry 30 of IMD 14, processing circuitry 50 of external charging device 20, or any one or more parts of the techniques described herein may be implemented by a processor of one of IMD 14, external charging device 20, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

Various examples have been described. These and other examples are within the scope of the following claims.

What is claimed is:

1. A system comprising:
    processing circuitry of at least one of an external charging device or an implantable medical device (IMD) configured to be implanted in a patient, the processing circuitry configured to:
        receive a signal sensed from the patient during charging of a rechargeable power source of the IMD;
        determine, based on the signal sensed from the patient, a sleep state of the patient; and
        adjust, based on the sleep state of the patient, charging of the rechargeable power source of the IMD.

2. The system of claim 1,
    wherein to determine, based on the signal sensed from the patient, the sleep state of the patient, the processing circuitry is configured to determine that the patient is asleep, and
    wherein to adjust, based on the sleep state of the patient, charging of the rechargeable power source of the IMD, the processing circuitry is configured to reduce a power level of the charging of the rechargeable power source of the IMD in response to determining that the patient is asleep.

3. The system of claim 1,
    wherein to determine, based on the signal sensed from the patient, the sleep state of the patient, the processing circuitry is configured to determine that the patient is asleep, and
    wherein to adjust, based on the sleep state of the patient, charging of the rechargeable power source of the IMD, the processing circuitry is configured to cease charging of the rechargeable power source of the IMD in response to determining that the patient is asleep.

4. The system of claim 1, wherein to determine, based on the signal sensed from the patient, the sleep state of the patient, the processing circuitry is configured to:
    determine, based on the signal sensed from the patient, an activity status of the patient; and
    determine, based on the activity status of the patient, the sleep state of the patient.

5. The system of claim 1, wherein to determine, based on the signal sensed from the patient, the sleep state of the patient, the processing circuitry is configured to:
    determine, based on the signal sensed from the patient, a posture of the patient; and
    determine, based on the posture of the patient, the sleep state of the patient.

6. The system of claim 1, wherein to receive the signal sensed from the patient, the processing circuitry is configured to receive, from one or more sensors external to the patient, the signal sensed from the patient during charging of the rechargeable power source of the IMD.

7. The system of claim 1, wherein to receive the signal sensed from the patient, the processing circuitry is configured to receive, from the IMD, the signal sensed from the patient during charging of the rechargeable power source of the IMD.

8. The system of claim 1, wherein to receive the signal sensed from the patient, the processing circuitry is configured to receive, according to a wireless communication protocol, the signal sensed from the patient during charging of the rechargeable power source of the IMD.

9. The system of claim 1, wherein the signal sensed from the patient during charging of the rechargeable power source of the IMD is representative of accelerometer data generated from activity of the patient during charging of the rechargeable power source of the IMD.

10. The system of claim 1, wherein the signal sensed from the patient during charging of the rechargeable power source of the IMD is indicative of at least one of a heart rate or a respiration rate of the patient during charging of the rechargeable power source of the IMD.

11. The system of claim 1, further comprising the external charging device, wherein the external charging device comprises comprising the processing circuitry.

12. The system of claim 1, further comprising the IMD, wherein the IMD comprises the processing circuitry.

13. A system comprising:
    an implantable medical device (IMD) configured to be implanted in a patient, the IMD comprising a rechargeable power source and first processing circuitry;
    an external charging device configured to charge the rechargeable power source of the IMD, the external charging device comprising second processing circuitry, wherein
    at least one of the first processing circuitry or the second processing circuitry is configured to:
        receive a signal sensed from the patient during charging, by the external charging device, of the rechargeable power source of the IMD;
        determine, based on the signal sensed from the patient, a sleep state of the patient; and
        control, based on the sleep state of the patient, charging of the rechargeable power source of the IMD.

14. A method comprising:
    receiving, by processing circuitry of at least one of an external charging device or an implantable medical device (IMD) implanted in a patient, a signal sensed from the patient during charging of a rechargeable power source of the IMD;
    determining, by the processing circuitry and based on the signal sensed from the patient, a sleep state of the patient; and
    adjusting, by the processing circuitry and based on the sleep state of the patient, charging of the rechargeable power source of the IMD.

15. The method of claim 14,
    wherein determining, based on the signal sensed from the patient, the sleep state of the patient comprises determining that the patient is asleep, and
    wherein adjusting, based on the sleep state of the patient, charging of the rechargeable power source of the IMD comprises reducing a power level of the charging of the rechargeable power source of the IMD in response to determining that the patient is asleep.

16. The method of claim 14,
    wherein determining, based on the signal sensed from the patient, the sleep state of the patient comprises determining that the patient is asleep, and wherein adjusting, based on the sleep state of the patient, charging of the rechargeable power source of the IMD comprises ceasing charging of the rechargeable power source of the IMD in response to determining that the patient is asleep.

17. The method of claim 14, wherein determining, based on the signal sensed from the patient, the sleep state of the patient comprises:
   determining, by the processing circuitry and based on the signal sensed from the patient, an activity status of the patient; and
   determining, by the processing circuitry and based on the activity status of the patient, the sleep state of the patient.

18. The method of claim 14, wherein determining, based on the signal sensed from the patient, the sleep state of the patient comprises:
   determining, by the processing circuitry and based on the signal sensed from the patient, a posture of the patient; and
   determining, by the processing circuitry and based on the posture of the patient, the sleep state of the patient.

19. The method of claim 14, wherein receiving the signal sensed from the patient comprises receiving, from one or more sensors external to the patient, the signal sensed from the patient during charging of the rechargeable power source of the IMD.

20. The method of claim 14, wherein receiving the signal sensed from the patient comprises receiving, from the IMD, the signal sensed from the patient during charging of the rechargeable power source of the IMD.

21. The method of claim 14, wherein receiving the signal sensed from the patient comprises receiving, according to a wireless communication protocol, the signal sensed from the patient during charging of the rechargeable power source of the IMD.

22. The method of claim 14, wherein the signal sensed from the patient during charging of the rechargeable power source of the IMD is representative of accelerometer data generated from activity of the patient during charging of the rechargeable power source of the IMD.

23. The method of claim 14, wherein the signal sensed from the patient during charging of the rechargeable power source of the IMD is indicative of at least one of a heart rate or a respiration rate of the patient during charging of the rechargeable power source of the IMD.

* * * * *